US010982245B2

(12) United States Patent
Kim et al.

(10) Patent No.: US 10,982,245 B2
(45) Date of Patent: Apr. 20, 2021

(54) O-SUCCINYL HOMOSERINE TRANSFERASE MUTANT AND METHOD FOR PRODUCING O-SUCCINYL HOMOSERINE USING SAME

(71) Applicant: CJ CheilJedang Corporation, Seoul (KR)

(72) Inventors: Kyungrim Kim, Seoul (KR); Jihyun Shim, Seoul (KR); Hyun Ah Kim, Seoul (KR); Yong Uk Shin, Seoul (KR); Peter Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/627,572

(22) PCT Filed: Jun. 29, 2018

(86) PCT No.: PCT/KR2018/007409

§ 371 (c)(1), (2) Date: Dec. 30, 2019

(87) PCT Pub. No.: WO2019/004780

PCT Pub. Date: Jan. 3, 2019

(65) Prior Publication Data

US 2020/0224228 A1 Jul. 16, 2020

(30) Foreign Application Priority Data

Jun. 30, 2017 (KR) ........................ 10-2017-0083439

(51) Int. Cl.
*C12P 13/06* (2006.01)
*C12P 13/12* (2006.01)
*C12R 1/15* (2006.01)

(52) U.S. Cl.
CPC ............... *C12P 13/06* (2013.01); *C12P 13/12* (2013.01); *C12R 1/15* (2013.01); *C12Y 203/01031* (2013.01)

(58) Field of Classification Search
CPC .... C12R 1/15; C12N 9/10; C12N 9/12; C12N 15/77; C07C 319/08; C12Y 203/01031; C12P 13/06; C12P 13/12
See application file for complete search history.

(56) References Cited

U.S. PATENT DOCUMENTS

2015/0211034 A1 7/2015 Kim et al.

FOREIGN PATENT DOCUMENTS

| | | | |
|---|---|---|---|
| KR | 1006200920000 | | 9/2006 |
| WO | 2006065095 | A1 | 6/2006 |
| WO | 2009096689 | A2 | 8/2009 |
| WO | 2010098629 | A2 | 9/2010 |
| WO | 2015060649 | A1 | 4/2015 |
| WO | 2016179545 | A1 | 11/2016 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Devereux, John et al. "A Comprehensive Set of Sequence Analysis Programs for the VAX" Nucleic Acids Research, vol. 12 No. 1, 1984, pp. 388-395.
Mordukhova, Elena A. et al. "Stabilized homoserine o-succinyltransferases (MetA) or L-methionine partially recovers the growth defect in *Escherichia coli* lacking ATP-dependent proteases or the Dnak chaperone" BMC Microbiology 2013, 13:179, pp. 13.
NCBI WP_011013793 homoserine O-acetyltransferase [Corynebacterium glutamicum] 1 page, Dec. 19, 2019.
Pearson, William R. et al. "Improved tools for biological sequence comparison" Proc. Natl. Acad. Sci. USA, vol. 85, pp. 2444-2448, Apr. 1988.
Rice, Peter et al. "EMBOSS: The European Molecular Biology Open Software Suite" TIG Jun. 2000, vol. 16, No. 6, pp. 276-277.
Needleman, Saul B. et al. "A General Method Applicable to the Search for Similarities in the Amino Acid Sequence of Two Proteins" J. Mol. Biol. (1970) 48, 443-453.

* cited by examiner

*Primary Examiner* — Ganapathirama Raghu
(74) *Attorney, Agent, or Firm* — Edwin S. Flores; Daniel J. Chalker; Chalker Flores, LLP

(57) ABSTRACT

The present disclosure relates to an O-succinyl homoserine transferase mutant, a polynucleotide encoding the same, a microorganism including the mutant, and a method of producing O-succinyl homoserine using the microorganism.

14 Claims, No Drawings

Specification includes a Sequence Listing.

SEQUENCE LISTING

```
<160> NUMBER OF SEQ ID NOS: 98

<210> SEQ ID NO 1
<211> LENGTH: 377
<212> TYPE: PRT
<213> ORGANISM: Corynebacterium glutamicum
<220> FEATURE:
<221> NAME/KEY: MISC_FEATURE
<223> OTHER INFORMATION: metX

<400> SEQUENCE: 1

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
```

-continued

```
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Leu Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 2
<211> LENGTH: 1134
<212> TYPE: DNA
<213> ORGANISM: Corynebacterium glutamicum
<220> FEATURE:
<221> NAME/KEY: misc_feature
<223> OTHER INFORMATION: metX

<400> SEQUENCE: 2

```
atgcccaccc tcgcgccttc aggtcaactt gaaatccaag cgatcggtga tgtctccacc      60

gaagccggag caatcattac aaacgctgaa atcgcctatc accgctgggg tgaataccgc     120

gtagataaag aaggacgcag caatgtcgtt ctcatcgaac acgccctcac tggagattcc     180

aacgcagccg attggtgggc tgacttgctc ggtcccggca aagccatcaa cactgatatt     240

tactgcgtga tctgtaccaa cgtcatcggt ggttgcaacg gttccaccgg acctggctcc     300

atgcatccag atggaaattt ctggggtaat cgcttccccg ccacgtccat tcgtgatcag     360
```

-continued

```
gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggcaaat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattttgt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134


<210> SEQ ID NO 3
<211> LENGTH: 379
<212> TYPE: PRT
<213> ORGANISM: Pseudomonas aeruginosa

<400> SEQUENCE: 3

Met Pro Thr Val Phe Pro Asp Asp Ser Val Gly Leu Val Ser Pro Gln
1               5                   10                  15

Thr Leu His Phe Asn Glu Pro Leu Glu Leu Thr Ser Gly Lys Ser Leu
            20                  25                  30

Ala Glu Tyr Asp Leu Val Ile Glu Thr Tyr Gly Glu Leu Asn Ala Thr
        35                  40                  45

Gln Ser Asn Ala Val Leu Ile Cys His Ala Leu Ser Gly His His His
    50                  55                  60

Ala Ala Gly Tyr His Ser Val Asp Glu Arg Lys Pro Gly Trp Trp Asp
65                  70                  75                  80

Ser Cys Ile Gly Pro Gly Lys Pro Ile Asp Thr Arg Lys Phe Phe Val
                85                  90                  95

Val Ala Leu Asn Asn Leu Gly Gly Cys Asn Gly Ser Ser Gly Pro Ala
            100                 105                 110

Ser Ile Asn Pro Ala Thr Gly Lys Val Tyr Gly Ala Asp Phe Pro Met
        115                 120                 125

Val Thr Val Glu Asp Trp Val His Ser Gln Ala Arg Leu Ala Asp Arg
    130                 135                 140

Leu Gly Ile Arg Gln Trp Ala Ala Val Val Gly Gly Ser Leu Gly Gly
145                 150                 155                 160

Met Gln Ala Leu Gln Trp Thr Ile Ser Tyr Pro Glu Arg Val Arg His
                165                 170                 175

Cys Leu Cys Ile Ala Ser Ala Pro Lys Leu Ser Ala Gln Asn Ile Ala
            180                 185                 190

Phe Asn Glu Val Ala Arg Gln Ala Ile Leu Ser Asp Pro Glu Phe Leu
        195                 200                 205

Gly Gly Tyr Phe Gln Glu Gln Gly Val Ile Pro Lys Arg Gly Leu Lys
    210                 215                 220

Leu Ala Arg Met Val Gly His Ile Thr Tyr Leu Ser Asp Asp Ala Met
225                 230                 235                 240
```

-continued

Gly Ala Lys Phe Gly Arg Val Leu Lys Thr Glu Lys Leu Asn Tyr Asp
245 250 255

Leu His Ser Val Glu Phe Gln Val Glu Ser Tyr Leu Arg Tyr Gln Gly
260 265 270

Glu Glu Phe Ser Thr Arg Phe Asp Ala Asn Thr Tyr Leu Leu Met Thr
275 280 285

Lys Ala Leu Asp Tyr Phe Asp Pro Ala Ala Ala His Gly Asp Asp Leu
290 295 300

Val Arg Thr Leu Glu Gly Val Glu Ala Asp Phe Cys Leu Met Ser Phe
305 310 315 320

Thr Thr Asp Trp Arg Phe Ser Pro Ala Arg Ser Arg Glu Ile Val Asp
325 330 335

Ala Leu Ile Ala Ala Lys Lys Asn Val Ser Tyr Leu Glu Ile Asp Ala
340 345 350

Pro Gln Gly His Asp Ala Phe Leu Met Pro Ile Pro Arg Tyr Leu Gln
355 360 365

Ala Phe Ser Gly Tyr Met Asn Arg Ile Ser Val
370 375

<210> SEQ ID NO 4
<211> LENGTH: 1140
<212> TYPE: DNA
<213> ORGANISM: Pseudomonas aeruginosa

<400> SEQUENCE: 4
atgcccacag tcttccccga cgactccgtc ggtctggtct ccccccagac gctgcacttc 60
aacgaaccgc tcgagctgac cagcggcaag tccctggccg agtacgacct ggtgatcgaa 120
acctacggcg agctgaatgc cacgcagagc aacgcggtgc tgatctgcca cgccctctcc 180
ggccaccacc acgccgccgg ctaccacagc gtcgacgagc gcaagccggg ctggtgggac 240
agctgcatcg gtccgggcaa gccgatcgac acccgcaagt tcttcgtcgt cgccctcaac 300
aacctcggcg gttgcaacgg atccagcggc cccgccagca tcaatccggc gaccggcaag 360
gtctacggcg cggacttccc gatggttacg gtggaagact gggtgcatag ccaggcgcgc 420
ctggcagacc gcctcggcat ccgccagtgg gccgcggtgg tcggcggcag cctcggcggc 480
atgcaggcgc tgcaatggac catcagctat cccgagcgcg tccgtcactg cctgtgcatc 540
gccagcgcgc cgaagctgtc ggcgcagaac atcgccttca acgaagtcgc ccggcaggcg 600
attctttccg accctgagtt cctcggcggc tacttccagg agcagggcgt gattcccaag 660
cgcggcctca agctggcgcg gatggtcggc catatcacct acctgtccga cgacgccatg 720
ggcgccaagt tcggccgtgt actgaagacc gagaagctca actacgacct gcacagcgtc 780
gagttccagg tcgagagtta cctgcgctac cagggcgagg agttctccac ccgcttcgac 840
gccaatacct acctgctgat gaccaaggcg ctggactact tcgaccccgc cgccgcccac 900
ggcgacgacc tggtgcgcac cctggagggc gtcgaggcgg acttctgcct gatgtccttc 960
accaccgact ggcgtttctc gccggcccgc tcgcgggaaa tcgtcgacgc cctgatcgcg 1020
gcgaaaaaga acgtcagcta cctggagatc gacgccccgc aaggccacga cgccttcctc 1080
atgccgatcc cccggtacct gcaagccttc agcggttaca tgaaccgcat cagcgtgtga 1140

<210> SEQ ID NO 5
<211> LENGTH: 28
<212> TYPE: DNA
<213> ORGANISM: Artificial Sequence
<220> FEATURE:

-continued

<223> OTHER INFORMATION: Synthetic primer

<400> SEQUENCE: 5
ggatcccctc gttgttcacc cagcaacc 28

<210> SEQ ID NO 6
<211> LENGTH: 30
<212> TYPE: DNA
<213> ORGANISM: Artificial Sequence
<220> FEATURE:
<223> OTHER INFORMATION: Synthic primer

<400> SEQUENCE: 6
ggatcccaaa gtcacaacta cttatgttag 30

<210> SEQ ID NO 7
<211> LENGTH: 35
<212> TYPE: DNA
<213> ORGANISM: Artificial Sequence
<220> FEATURE:
<223> OTHER INFORMATION: Synthetic primer

<400> SEQUENCE: 7
acgcgccagc gcctggaaca tcggcattca atccg 35

<210> SEQ ID NO 8
<211> LENGTH: 35
<212> TYPE: DNA
<213> ORGANISM: Artificial Sequence
<220> FEATURE:
<223> OTHER INFORMATION: Synthetic primer

<400> SEQUENCE: 8
cggattgaat gccgatgttc caggcgctgg cgcgt 35

<210> SEQ ID NO 9
<211> LENGTH: 33
<212> TYPE: DNA
<213> ORGANISM: Artificial Sequence
<220> FEATURE:
<223> OTHER INFORMATION: Synthetic primer

<400> SEQUENCE: 9
gtagataccg atattcggta cccctaccac cag 33

<210> SEQ ID NO 10
<211> LENGTH: 33
<212> TYPE: DNA
<213> ORGANISM: Artificial Sequence
<220> FEATURE:
<223> OTHER INFORMATION: Synthetic primer

<400> SEQUENCE: 10
ctggtggtag gggtaccgaa tatcggtatc tac 33

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
tctagatgcg ctgattatct cacc 24

<210> SEQ ID NO 12
<211> LENGTH: 40
<212> TYPE: DNA
<213> ORGANISM: Artificial Sequence
<220> FEATURE:
<223> OTHER INFORMATION: Synthetic primer

<400> SEQUENCE: 12
actggtgggt catggttgca tatgagatca actcctgtaa 40

<210> SEQ ID NO 13
<211> LENGTH: 40
<212> TYPE: DNA
<213> ORGANISM: Artificial Sequence
<220> FEATURE:
<223> OTHER INFORMATION: Synthetic primer

<400> SEQUENCE: 13
ttacaggagt tgatctcata tgcaaccatg acccaccagt 40

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
tctagacctt gaagttcttg actg 24

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
tctagaagta gcgttgctgt acac 24

<210> SEQ ID NO 16
<211> LENGTH: 43
<212> TYPE: DNA
<213> ORGANISM: Artificial Sequence
<220> FEATURE:
<223> OTHER INFORMATION: Synthetic primer

<400> SEQUENCE: 16
atcaatggtc tcgatgccca tatggcattt ggaggtcctt aag 43

<210> SEQ ID NO 17
<211> LENGTH: 43
<212> TYPE: DNA
<213> ORGANISM: Artificial Sequence
<220> FEATURE:
<223> OTHER INFORMATION: Synthetic primer

<400> SEQUENCE: 17
cttaaggacc tccaaatgcc atatgggcat cgagaccatt gat 43

<210> SEQ ID NO 18
<211> LENGTH: 24
<212> TYPE: DNA
<213> ORGANISM: Artificial Sequence
<220> FEATURE:
<223> OTHER INFORMATION: Synthetic primer -continued

<400> SEQUENCE: 18
tctagatgga accgttgcaa ccac 24

<210> SEQ ID NO 19
<211> LENGTH: 421
<212> TYPE: PRT
<213> ORGANISM: Corynebacterium glutamicum
<220> FEATURE:
<221> NAME/KEY: MISC_FEATURE
<223> OTHER INFORMATION: lysC

<400> SEQUENCE: 19

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
```

-continued

```
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420


<210> SEQ ID NO 20
<211> LENGTH: 1266
<212> TYPE: DNA
<213> ORGANISM: Corynebacterium glutamicum
<220> FEATURE:
<221> NAME/KEY: misc_feature
<223> OTHER INFORMATION: lysC

<400> SEQUENCE: 20

atggccctgg tcgtacagaa atatggcggt tcctcgcttg agagtgcgga acgcattaga      60

aacgtcgctg aacggatcgt tgccaccaag aaggctggaa atgatgtcgt ggttgtctgc     120

tccgcaatgg gagacaccac ggatgaactt ctagaacttg cagcggcagt gaatcccgtt     180

ccgccagctc gtgaaatgga tatgctcctg actgctggtg agcgtatttc taacgctctc     240

gtcgccatgg ctattgagtc ccttggcgca gaagcccaat ctttcacggg ctctcaggct     300

ggtgtgctca ccaccgagcg ccacggaaac gcacgcattg ttgatgtcac tccaggtcgt     360

gtgcgtgaag cactcgatga gggcaagatc tgcattgttg ctggtttcca gggtgttaat     420

aaagaaaccc gcgatgtcac cacgttgggt cgtggtggtt ctgacaccac tgcagttgcg     480

ttggcagctg ctttgaacgc tgatgtgtgt gagatttact cggacgttga cggtgtgtat     540

accgctgacc cgcgcatcgt tcctaatgca cagaagctgg aaaagctcag cttcgaagaa     600

atgctggaac ttgctgctgt tggctccaag attttggtgc tgcgcagtgt tgaatacgct     660

cgtgcattca atgtgccact tcgcgtacgc tcgtcttata gtaatgatcc cggcactttg     720

attgccggct ctatggagga tattcctgtg gaagaagcag tccttaccgg tgtcgcaacc     780

gacaagtccg aagccaaagt aaccgttctg ggtatttccg ataagccagg cgaggctgcg     840

aaggttttcc gtgcgttggc tgatgcagaa atcaacattg acatggttct gcagaacgtc     900

tcttctgtag aagacggcac caccgacatc accttcacct gccctcgttc cgacggccgc     960

cgcgcgatgg agatcttgaa gaagcttcag gttcagggca actggaccaa tgtgctttac    1020

gacgaccagg tcggcaaagt ctccctcgtg ggtgctggca tgaagtctca cccaggtgtt    1080

accgcagagt tcatggaagc tctgcgcgat gtcaacgtga acatcgaatt gatttccacc    1140

tctgagattc gtatttccgt gctgatccgt gaagatgatc tggatgctgc tgcacgtgca    1200

ttgcatgagc agttccagct gggcggcgaa gacgaagccg tcgtttatgc aggcaccgga    1260

cgctaa                                                               1266


<210> SEQ ID NO 21
<211> LENGTH: 29
<212> TYPE: DNA
<213> ORGANISM: Artificial Sequence
<220> FEATURE:
<223> OTHER INFORMATION: Synthetic primer
```

<400> SEQUENCE: 21
tcctctagag ctgcgcagtg ttgaatacg 29

<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
caccgacatc atcttcacct gcc 23

<210> SEQ ID NO 23
<211> LENGTH: 23
<212> TYPE: DNA
<213> ORGANISM: Artificial Sequence
<220> FEATURE:
<223> OTHER INFORMATION: Synthetic primer

<400> SEQUENCE: 23
ggcaggtgaa gatgatgtcg gtg 23

<210> SEQ ID NO 24
<211> LENGTH: 29
<212> TYPE: DNA
<213> ORGANISM: Artificial Sequence
<220> FEATURE:
<223> OTHER INFORMATION: Synthetic primer

<400> SEQUENCE: 24
gactctagag ttcacctcag agacgatta 29

<210> SEQ ID NO 25
<211> LENGTH: 421
<212> TYPE: PRT
<213> ORGANISM: Corynebacterium glutamicum
<220> FEATURE:
<221> NAME/KEY: MISC_FEATURE
<223> OTHER INFORMATION: lysC variant (T311I)

<400> SEQUENCE: 25

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140
```

-continued

```
Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420
```

<210> SEQ ID NO 26
<211> LENGTH: 1266
<212> TYPE: DNA
<213> ORGANISM: Corynebacterium glutamicum
<220> FEATURE:
<221> NAME/KEY: misc_feature
<223> OTHER INFORMATION: lysC variant (T311I)

<400> SEQUENCE: 26

```
atggccctgg tcgtacagaa atatggcggt tcctcgcttg agagtgcgga acgcattaga      60

aacgtcgctg aacggatcgt tgccaccaag aaggctggaa atgatgtcgt ggttgtctgc     120

tccgcaatgg gagacaccac ggatgaactt ctagaacttg cagcggcagt gaatcccgtt     180

ccgccagctc gtgaaatgga tatgctcctg actgctggtg agcgtatttc taacgctctc     240

gtcgccatgg ctattgagtc ccttggcgca gaagcccaat ctttcacggg ctctcaggct     300

ggtgtgctca ccaccgagcg ccacggaaac gcacgcattg ttgatgtcac tccaggtcgt     360

gtgcgtgaag cactcgatga gggcaagatc tgcattgttg ctggtttcca gggtgttaat     420
```

-continued

```
aaagaaaccc gcgatgtcac cacgttgggt cgtggtggtt ctgacaccac tgcagttgcg    480

ttggcagctg ctttgaacgc tgatgtgtgt gagatttact cggacgttga cggtgtgtat    540

accgctgacc cgcgcatcgt tcctaatgca cagaagctgg aaaagctcag cttcgaagaa    600

atgctggaac ttgctgctgt tggctccaag attttggtgc tgcgcagtgt tgaatacgct    660

cgtgcattca atgtgccact tcgcgtacgc tcgtcttata gtaatgatcc cggcactttg    720

attgccggct ctatggagga tattcctgtg gaagaagcag tccttaccgg tgtcgcaacc    780

gacaagtccg aagccaaagt aaccgttctg ggtatttccg ataagccagg cgaggctgcg    840

aaggttttcc gtgcgttggc tgatgcagaa atcaacattg acatggttct gcagaacgtc    900

tcttctgtag aagacggcac caccgacatc atcttcacct gccctcgttc cgacggccgc    960

cgcgcgatgg agatcttgaa gaagcttcag gttcagggca actggaccaa tgtgctttac   1020

gacgaccagg tcggcaaagt ctccctcgtg ggtgctggca tgaagtctca cccaggtgtt   1080

accgcagagt tcatggaagc tctgcgcgat gtcaacgtga acatcgaatt gatttccacc   1140

tctgagattc gtatttccgt gctgatccgt gaagatgatc tggatgctgc tgcacgtgca   1200

ttgcatgagc agttccagct gggcggcgaa gacgaagccg tcgtttatgc aggcaccgga   1260

cgctaa                                                               1266


<210> SEQ ID NO 27
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176F,L313R

<400> SEQUENCE: 27

acgcgccagc gcctggttta tcggcattca atccg                                35


<210> SEQ ID NO 28
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176F,L313R

<400> SEQUENCE: 28

cggattgaat gccgataaac caggcgctgg cgcgt                                35


<210> SEQ ID NO 29
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176S,L313R

<400> SEQUENCE: 29

acgcgccagc gcctggtcta tcggcattca atccg                                35


<210> SEQ ID NO 30
<211> LENGTH: 35
<212> TYPE: DNA
```

<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176S,L313R

<400> SEQUENCE: 30
cggattgaat gccgatagac caggcgctgg cgcgt 35

<210> SEQ ID NO 31
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176Y,L313R

<400> SEQUENCE: 31
acgcgccagc gcctggtata tcggcattca atccg 35

<210> SEQ ID NO 32
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176Y,L313R

<400> SEQUENCE: 32
cggattgaat gccgatatac caggcgctgg cgcgt 35

<210> SEQ ID NO 33
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176C,L313R

<400> SEQUENCE: 33
acgcgccagc gcctggtgca tcggcattca atccg 35

<210> SEQ ID NO 34
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176C,L313R

<400> SEQUENCE: 34
cggattgaat gccgatgcac caggcgctgg cgcgt 35

<210> SEQ ID NO 35
<211> LENGTH: 35
<212> TYPE: DNA
<213> ORGANISM: Artificial Sequence
<220> FEATURE:
<223> OTHER INFORMATION: Synthetic primer
<220> FEATURE:

```
<221> NAME/KEY: misc_feature
<223> OTHER INFORMATION: Forward primer for Q176P,L313R

<400> SEQUENCE: 35

acgcgccagc gcctggccaa tcggcattca atccg                              35


<210> SEQ ID NO 36
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176P,L313R

<400> SEQUENCE: 36

cggattgaat gccgattggc caggcgctgg cgcgt                              35


<210> SEQ ID NO 37
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer Q176H,L313R

<400> SEQUENCE: 37

acgcgccagc gcctggcaca tcggcattca atccg                              35


<210> SEQ ID NO 38
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176H,L313R

<400> SEQUENCE: 38

cggattgaat gccgatgtgc caggcgctgg cgcgt                              35


<210> SEQ ID NO 39
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176L,L313R

<400> SEQUENCE: 39

acgcgccagc gcctggctca tcggcattca atccg                              35


<210> SEQ ID NO 40
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176L,L313R

<400> SEQUENCE: 40
```

cggattgaat gccgatgagc caggcgctgg cgcgt 35

<210> SEQ ID NO 41
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176I,L313R

<400> SEQUENCE: 41
acgcgccagc gcctggatta tcggcattca atccg 35

<210> SEQ ID NO 42
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176I,L313R

<400> SEQUENCE: 42
cggattgaat gccgataatc caggcgctgg cgcgt 35

<210> SEQ ID NO 43
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176T,L313R

<400> SEQUENCE: 43
acgcgccagc gcctggacta tcggcattca atccg 35

<210> SEQ ID NO 44
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176T,L313R

<400> SEQUENCE: 44
cggattgaat gccgatagtc caggcgctgg cgcgt 35

<210> SEQ ID NO 45
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176R,L313R

<400> SEQUENCE: 45
acgcgccagc gcctggcgca tcggcattca atccg 35

<210> SEQ ID NO 46
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176R,L313R

<400> SEQUENCE: 46
cggattgaat gccgatgcgc caggcgctgg cgcgt 35

<210> SEQ ID NO 47
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176K,L313R

<400> SEQUENCE: 47
acgcgccagc gcctggaaaa tcggcattca atccg 35

<210> SEQ ID NO 48
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176K,L313R

<400> SEQUENCE: 48
cggattgaat gccgattttc caggcgctgg cgcgt 35

<210> SEQ ID NO 49
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176V,L313R

<400> SEQUENCE: 49
acgcgccagc gcctgggtta tcggcattca atccg 35

<210> SEQ ID NO 50
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176V,L313R

<400> SEQUENCE: 50
cggattgaat gccgataacc caggcgctgg cgcgt 35

<210> SEQ ID NO 51
<211> LENGTH: 35
<212> TYPE: DNA
<213> ORGANISM: Artificial Sequence -continued
<220> FEATURE:
<223> OTHER INFORMATION: Synthetic primer
<220> FEATURE:
<221> NAME/KEY: misc_feature
<223> OTHER INFORMATION: Forward primer for Q176A,L313R

<400> SEQUENCE: 51
acgcgccagc gcctgggcaa tcggcattca atccg 35

<210> SEQ ID NO 52
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176A,L313R

<400> SEQUENCE: 52
cggattgaat gccgattgcc caggcgctgg cgcgt 35

<210> SEQ ID NO 53
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176D,L313R

<400> SEQUENCE: 53
acgcgccagc gcctgggaca tcggcattca atccg 35

<210> SEQ ID NO 54
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176D,L313R

<400> SEQUENCE: 54
cggattgaat gccgatgtcc caggcgctgg cgcgt 35

<210> SEQ ID NO 55
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176E,L313R

<400> SEQUENCE: 55
acgcgccagc gcctgggaga tcggcattca atccg 35

<210> SEQ ID NO 56
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176E,L313R

<400> SEQUENCE: 56
cggattgaat gccgatctcc caggcgctgg cgcgt 35

<210> SEQ ID NO 57
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176G,L313R

<400> SEQUENCE: 57
acgcgccagc gcctggggca tcggcattca atccg 35

<210> SEQ ID NO 58
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176G,L313R

<400> SEQUENCE: 58
cggattgaat gccgatgccc caggcgctgg cgcgt 35

<210> SEQ ID NO 59
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Forward primer for Q176W,L313R

<400> SEQUENCE: 59
acgcgccagc gcctggtgga tcggcattca atccg 35

<210> SEQ ID NO 60
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Reverse primer for Q176W,L313R

<400> SEQUENCE: 60
cggattgaat gccgatccac caggcgctgg cgcgt 35

<210> SEQ ID NO 61
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: metX L313R

<400> SEQUENCE: 61

-continued

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 62
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: metX L313R

<400> SEQUENCE: 62
atgcccaccc tcgcgccttc aggtcaactt gaaatccaag cgatcggtga tgtctccacc 60
gaagccggag caatcattac aaacgctgaa atcgcctatc accgctgggg tgaataccgc 120
gtagataaag aaggacgcag caatgtcgtt ctcatcgaac acgccctcac tggagattcc 180
aacgcagccg attggtgggc tgacttgctc ggtcccggca aagccatcaa cactgatatt 240
tactgcgtga tctgtaccaa cgtcatcggt ggttgcaacg gttccaccgg acctggctcc 300
atgcatccag atggaaattt ctggggtaat cgcttccccg ccacgtccat tcgtgatcag 360
gtaaacgccg aaaaacaatt cctcgacgca ctcggcatca ccacggtcgc cgcagtactt 420
ggtggttcca tgggtggtgc ccgcacccta gagtgggccg caatgtaccc agaaactgtt 480
ggcgcagctg ctgttcttgc agtttctgca cgcgccagcg cctggcaaat cggcattcaa 540
tccgcccaaa ttaaggcgat tgaaaacgac caccactggc acgaaggcaa ctactacgaa 600
tccggctgca acccagccac cggactcggc gccgcccgac gcatcgccca cctcacctac 660
cgtggcgaac tagaaatcga cgaacgcttc ggcaccaaag cccaaaagaa cgaaaaccca 720
ctcggtccct accgcaagcc cgaccagcgc ttcgccgtgg aatcctactt ggactaccaa 780
gcagacaagc tagtacagcg tttcgacgcc ggctcctacg tcttgctcac cgacgccctc 840
aaccgccacg acattggtcg cgaccgcgga ggcctcaaca aggcactcga atccatcaaa 900
gttccagtcc ttgtcgcagg cgtagatacc gatattcggt acccctacca ccagcaagaa 960
cacctctcca gaaacctggg aaatctactg gcaatggcaa aaatcgtatc ccctgtcggc 1020
cacgatgctt tcctcaccga aagccgccaa atggatcgca tcgtgaggaa cttcttcagc 1080
ctcatctccc cagacgaaga caacccttcg acctacatcg agttctacat ctaa 1134

<210> SEQ ID NO 63
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: metX Q176N_L313R

<400> SEQUENCE: 63

Met Pro Thr Leu Ala Pro Ser Gly Gln Leu Glu Ile Gln Ala Ile Gly
1 5 10 15

Asp Val Ser Thr Glu Ala Gly Ala Ile Ile Thr Asn Ala Glu Ile Ala
20 25 30

Tyr His Arg Trp Gly Glu Tyr Arg Val Asp Lys Glu Gly Arg Ser Asn
35 40 45

Val Val Leu Ile Glu His Ala Leu Thr Gly Asp Ser Asn Ala Ala Asp
50 55 60

Trp Trp Ala Asp Leu Leu Gly Pro Gly Lys Ala Ile Asn Thr Asp Ile
65 70 75 80

Tyr Cys Val Ile Cys Thr Asn Val Ile Gly Gly Cys Asn Gly Ser Thr
85 90 95

Gly Pro Gly Ser Met His Pro Asp Gly Asn Phe Trp Gly Asn Arg Phe
100 105 110

Pro Ala Thr Ser Ile Arg Asp Gln Val Asn Ala Glu Lys Gln Phe Leu

```
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Asn
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375


<210> SEQ ID NO 64
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: metX Q176N_L313R

<400> SEQUENCE: 64

atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480
```

-continued

```
ggcgcagctg ctgttcttgc agtttctgca cgcgccagcg cctggaacat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

<210> SEQ ID NO 65
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176F,L313R

<400> SEQUENCE: 65

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Phe
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240
```

-continued

```
Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375


<210> SEQ ID NO 66
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176F,L313R

<400> SEQUENCE: 66

atgcccaccc tcgcgccttc aggtcaactt gaaatccaag cgatcggtga tgtctccacc      60

gaagccggag caatcattac aaacgctgaa atcgcctatc accgctgggg tgaataccgc     120

gtagataaag aaggacgcag caatgtcgtt ctcatcgaac acgccctcac tggagattcc     180

aacgcagccg attggtgggc tgacttgctc ggtcccggca aagccatcaa cactgatatt     240

tactgcgtga tctgtaccaa cgtcatcggt ggttgcaacg gttccaccgg acctggctcc     300

atgcatccag atggaaattt ctggggtaat cgcttccccg ccacgtccat tcgtgatcag     360

gtaaacgccg aaaaacaatt cctcgacgca ctcggcatca ccacggtcgc cgcagtactt     420

ggtggttcca tgggtggtgc ccgcacccta gagtgggccg caatgtaccc agaaactgtt     480

ggcgcagctg ctgttcttgc agtttctgca cgcgccagcg cctggtttat cggcattcaa     540

tccgcccaaa ttaaggcgat tgaaaacgac caccactggc acgaaggcaa ctactacgaa     600

tccggctgca acccagccac cggactcggc gccgcccgac gcatcgccca cctcacctac     660

cgtggcgaac tagaaatcga cgaacgcttc ggcaccaaag cccaaaagaa cgaaaaccca     720

ctcggtccct accgcaagcc cgaccagcgc ttcgccgtgg aatcctactt ggactaccaa     780

gcagacaagc tagtacagcg tttcgacgcc ggctcctacg tcttgctcac cgacgccctc     840

aaccgccacg acattggtcg cgaccgcgga ggcctcaaca aggcactcga atccatcaaa     900

gttccagtcc ttgtcgcagg cgtagatacc gatattcggt acccctacca ccagcaagaa     960

cacctctcca gaaacctggg aaatctactg gcaatggcaa aaatcgtatc ccctgtcggc    1020

cacgatgctt tcctcaccga aagccgccaa atggatcgca tcgtgaggaa cttcttcagc    1080

ctcatctccc cagacgaaga caacccttcg acctacatcg agttctacat ctaa          1134
```

<210> SEQ ID NO 67
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176S,L313R

<400> SEQUENCE: 67

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Ser
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350
```

```
Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375


<210> SEQ ID NO 68
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176S,L313R

<400> SEQUENCE: 68

atgcccaccc tcgcgccttc aggtcaactt gaaatccaag cgatcggtga tgtctccacc      60

gaagccggag caatcattac aaacgctgaa atcgcctatc accgctgggg tgaataccgc     120

gtagataaag aaggacgcag caatgtcgtt ctcatcgaac acgccctcac tggagattcc     180

aacgcagccg attggtgggc tgacttgctc ggtcccggca aagccatcaa cactgatatt     240

tactgcgtga tctgtaccaa cgtcatcggt ggttgcaacg gttccaccgg acctggctcc     300

atgcatccag atggaaattt ctggggtaat cgcttccccg ccacgtccat tcgtgatcag     360

gtaaacgccg aaaaacaatt cctcgacgca ctcggcatca ccacggtcgc cgcagtactt     420

ggtggttcca tgggtggtgc ccgcacccta gagtgggccg caatgtaccc agaaactgtt     480

ggcgcagctg ctgttcttgc agtttctgca cgcgccagcg cctggtctat cggcattcaa     540

tccgcccaaa ttaaggcgat tgaaaacgac caccactggc acgaaggcaa ctactacgaa     600

tccggctgca acccagccac cggactcggc gccgcccgac gcatcgccca cctcacctac     660

cgtggcgaac tagaaatcga cgaacgcttc ggcaccaaag cccaaaagaa cgaaaaccca     720

ctcggtccct accgcaagcc cgaccagcgc ttcgccgtgg aatcctactt ggactaccaa     780

gcagacaagc tagtacagcg tttcgacgcc ggctcctacg tcttgctcac cgacgccctc     840

aaccgccacg acattggtcg cgaccgcgga ggcctcaaca aggcactcga atccatcaaa     900

gttccagtcc ttgtcgcagg cgtagatacc gatattcggt accccctacca ccagcaagaa     960

cacctctcca gaaacctggg aaatctactg gcaatggcaa aaatcgtatc ccctgtcggc    1020

cacgatgctt tcctcaccga aagccgccaa atggatcgca tcgtgaggaa cttcttcagc    1080

ctcatctccc cagacgaaga caacccttcg acctacatcg agttctacat ctaa         1134


<210> SEQ ID NO 69
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176Y,L313R

<400> SEQUENCE: 69

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45
```

-continued

```
Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Tyr
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 70
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176Y,L313R

<400> SEQUENCE: 70

```
atgcccaccc tcgcgccttc aggtcaactt gaaatccaag cgatcggtga tgtctccacc      60

gaagccggag caatcattac aaacgctgaa atcgcctatc accgctgggg tgaataccgc     120
```

```
gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggtatat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

<210> SEQ ID NO 71
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176C,L313R

<400> SEQUENCE: 71

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Cys
```

165 170 175

Ile Gly Ile Gln Ser Ala Gln Ile Lys Ala Ile Glu Asn Asp His His
180 185 190

Trp His Glu Gly Asn Tyr Tyr Glu Ser Gly Cys Asn Pro Ala Thr Gly
195 200 205

Leu Gly Ala Ala Arg Arg Ile Ala His Leu Thr Tyr Arg Gly Glu Leu
210 215 220

Glu Ile Asp Glu Arg Phe Gly Thr Lys Ala Gln Lys Asn Glu Asn Pro
225 230 235 240

Leu Gly Pro Tyr Arg Lys Pro Asp Gln Arg Phe Ala Val Glu Ser Tyr
245 250 255

Leu Asp Tyr Gln Ala Asp Lys Leu Val Gln Arg Phe Asp Ala Gly Ser
260 265 270

Tyr Val Leu Leu Thr Asp Ala Leu Asn Arg His Asp Ile Gly Arg Asp
275 280 285

Arg Gly Gly Leu Asn Lys Ala Leu Glu Ser Ile Lys Val Pro Val Leu
290 295 300

Val Ala Gly Val Asp Thr Asp Ile Arg Tyr Pro Tyr His Gln Gln Glu
305 310 315 320

His Leu Ser Arg Asn Leu Gly Asn Leu Leu Ala Met Ala Lys Ile Val
325 330 335

Ser Pro Val Gly His Asp Ala Phe Leu Thr Glu Ser Arg Gln Met Asp
340 345 350

Arg Ile Val Arg Asn Phe Phe Ser Leu Ile Ser Pro Asp Glu Asp Asn
355 360 365

Pro Ser Thr Tyr Ile Glu Phe Tyr Ile
370 375

<210> SEQ ID NO 72
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176C,L313R

<400> SEQUENCE: 72
atgcccaccc tcgcgccttc aggtcaactt gaaatccaag cgatcggtga tgtctccacc 60
gaagccggag caatcattac aaacgctgaa atcgcctatc accgctgggg tgaataccgc 120
gtagataaag aaggacgcag caatgtcgtt ctcatcgaac acgccctcac tggagattcc 180
aacgcagccg attggtgggc tgacttgctc ggtcccggca aagccatcaa cactgatatt 240
tactgcgtga tctgtaccaa cgtcatcggt ggttgcaacg gttccaccgg acctggctcc 300
atgcatccag atggaaattt ctggggtaat cgcttccccg ccacgtccat tcgtgatcag 360
gtaaacgccg aaaaacaatt cctcgacgca ctcggcatca ccacggtcgc cgcagtactt 420
ggtggttcca tgggtggtgc ccgcacccta gagtgggccg caatgtaccc agaaactgtt 480
ggcgcagctg ctgttcttgc agtttctgca cgcgccagcg cctggtgtat cggcattcaa 540
tccgcccaaa ttaaggcgat tgaaaacgac caccactggc acgaaggcaa ctactacgaa 600
tccggctgca acccagccac cggactcggc gccgcccgac gcatcgccca cctcacctac 660
cgtggcgaac tagaaatcga cgaacgcttc ggcaccaaag cccaaaagaa cgaaaaccca 720
ctcggtccct accgcaagcc cgaccagcgc ttcgccgtgg aatcctactt ggactaccaa 780
gcagacaagc tagtacagcg tttcgacgcc ggctcctacg tcttgctcac cgacgccctc 840
aaccgccacg acattggtcg cgaccgcgga ggcctcaaca aggcactcga atccatcaaa 900
gttccagtcc ttgtcgcagg cgtagatacc gatattcggt acccctacca ccagcaagaa 960
cacctctcca gaaacctggg aaatctactg gcaatggcaa aaatcgtatc ccctgtcggc 1020
cacgatgctt tcctcaccga aagccgccaa atggatcgca tcgtgaggaa cttcttcagc 1080
ctcatctccc cagacgaaga caacccttcg acctacatcg agttctacat ctaa 1134

<210> SEQ ID NO 73
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176P,L313R

<400> SEQUENCE: 73

Met Pro Thr Leu Ala Pro Ser Gly Gln Leu Glu Ile Gln Ala Ile Gly
1 5 10 15

Asp Val Ser Thr Glu Ala Gly Ala Ile Ile Thr Asn Ala Glu Ile Ala
20 25 30

Tyr His Arg Trp Gly Glu Tyr Arg Val Asp Lys Glu Gly Arg Ser Asn
35 40 45

Val Val Leu Ile Glu His Ala Leu Thr Gly Asp Ser Asn Ala Ala Asp
50 55 60

Trp Trp Ala Asp Leu Leu Gly Pro Gly Lys Ala Ile Asn Thr Asp Ile
65 70 75 80

Tyr Cys Val Ile Cys Thr Asn Val Ile Gly Gly Cys Asn Gly Ser Thr
85 90 95

Gly Pro Gly Ser Met His Pro Asp Gly Asn Phe Trp Gly Asn Arg Phe
100 105 110

Pro Ala Thr Ser Ile Arg Asp Gln Val Asn Ala Glu Lys Gln Phe Leu
115 120 125

Asp Ala Leu Gly Ile Thr Thr Val Ala Ala Val Leu Gly Gly Ser Met
130 135 140

Gly Gly Ala Arg Thr Leu Glu Trp Ala Ala Met Tyr Pro Glu Thr Val
145 150 155 160

Gly Ala Ala Ala Val Leu Ala Val Ser Ala Arg Ala Ser Ala Trp Pro
165 170 175

Ile Gly Ile Gln Ser Ala Gln Ile Lys Ala Ile Glu Asn Asp His His
180 185 190

Trp His Glu Gly Asn Tyr Tyr Glu Ser Gly Cys Asn Pro Ala Thr Gly
195 200 205

Leu Gly Ala Ala Arg Arg Ile Ala His Leu Thr Tyr Arg Gly Glu Leu
210 215 220

Glu Ile Asp Glu Arg Phe Gly Thr Lys Ala Gln Lys Asn Glu Asn Pro
225 230 235 240

Leu Gly Pro Tyr Arg Lys Pro Asp Gln Arg Phe Ala Val Glu Ser Tyr
245 250 255

Leu Asp Tyr Gln Ala Asp Lys Leu Val Gln Arg Phe Asp Ala Gly Ser
260 265 270

Tyr Val Leu Leu Thr Asp Ala Leu Asn Arg His Asp Ile Gly Arg Asp
275 280 285

```
Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 74
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176P,L313R

<400> SEQUENCE: 74

```
atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggccaat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

<210> SEQ ID NO 75
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

<223> OTHER INFORMATION: Q176H,L313R

<400> SEQUENCE: 75

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp His
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 76
<211> LENGTH: 1134

<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176H,L313R

<400> SEQUENCE: 76

```
atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggcacat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

<210> SEQ ID NO 77
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176L,L313R

<400> SEQUENCE: 77

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95
```

```
Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Leu
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 78
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176L,L313R

<400> SEQUENCE: 78

```
atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360
```

```
gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggctcat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134


<210> SEQ ID NO 79
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176I,L313R

<400> SEQUENCE: 79

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Ile
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
```

```
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375


<210> SEQ ID NO 80
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176I,L313R

<400> SEQUENCE: 80

atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggattat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020
```

-continued

```
cacgatgctt tcctcaccga aagccgccaa atggatcgca tcgtgaggaa cttcttcagc   1080

ctcatctccc cagacgaaga caacccttcg acctacatcg agttctacat ctaa         1134


<210> SEQ ID NO 81
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176T,L313R

<400> SEQUENCE: 81

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Thr
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335
```

```
Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 82
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176T,L313R

<400> SEQUENCE: 82

```
atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggactat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt accccctacca ccagcaagaa    960

cacctctcca gaaacctggg aaatctactg gcaatggcaa aaatcgtatc cctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa          1134
```

<210> SEQ ID NO 83
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176R,L313R

<400> SEQUENCE: 83

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30
```

```
Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Arg
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 84
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176R,L313R

<400> SEQUENCE: 84

```
atgcccaccc tcgcgccttc aggtcaactt gaaatccaag cgatcggtga tgtctccacc     60
gaagccggag caatcattac aaacgctgaa atcgcctatc accgctgggg tgaataccgc    120
gtagataaag aaggacgcag caatgtcgtt ctcatcgaac acgccctcac tggagattcc    180
aacgcagccg attggtgggc tgacttgctc ggtcccggca aagccatcaa cactgatatt    240
tactgcgtga tctgtaccaa cgtcatcggt ggttgcaacg gttccaccgg acctggctcc    300
atgcatccag atggaaattt ctggggtaat cgcttccccg ccacgtccat tcgtgatcag    360
gtaaacgccg aaaaacaatt cctcgacgca ctcggcatca ccacggtcgc cgcagtactt    420
ggtggttcca tgggtggtgc ccgcacccta gagtgggccg caatgtaccc agaaactgtt    480
ggcgcagctg ctgttcttgc agtttctgca cgcgccagcg cctggcgcat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattcggt acccctacca ccagcaagaa    960
cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caacccttcg acctacatcg agttctacat ctaa         1134
```

<210> SEQ ID NO 85
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176K,L313R

<400> SEQUENCE: 85

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140
```

-continued

```
Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Lys
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 86
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176V,L313R
<220> FEATURE:
<221> NAME/KEY: misc_feature
<223> OTHER INFORMATION: Q176K,L313R

<400> SEQUENCE: 86

```
atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggaaaat cggcattcaa    540
```

-continued

```
tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134


<210> SEQ ID NO 87
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176V,L313R

<400> SEQUENCE: 87

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Val
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
```

```
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375
```

<210> SEQ ID NO 88
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176V,L313R

<400> SEQUENCE: 88

```
atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctgggttat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

<210> SEQ ID NO 89

<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176A,L313R

<400> SEQUENCE: 89

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Ala
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365
```

Pro Ser Thr Tyr Ile Glu Phe Tyr Ile
370 375

<210> SEQ ID NO 90
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176A,L313R

<400> SEQUENCE: 90
atgcccaccc tcgcgccttc aggtcaactt gaaatccaag cgatcggtga tgtctccacc 60
gaagccggag caatcattac aaacgctgaa atcgcctatc accgctgggg tgaataccgc 120
gtagataaag aaggacgcag caatgtcgtt ctcatcgaac acgccctcac tggagattcc 180
aacgcagccg attggtgggc tgacttgctc ggtcccggca aagccatcaa cactgatatt 240
tactgcgtga tctgtaccaa cgtcatcggt ggttgcaacg gttccaccgg acctggctcc 300
atgcatccag atggaaattt ctggggtaat cgcttccccg ccacgtccat tcgtgatcag 360
gtaaacgccg aaaaacaatt cctcgacgca ctcggcatca ccacggtcgc cgcagtactt 420
ggtggttcca tgggtggtgc ccgcacccta gagtgggccg caatgtaccc agaaactgtt 480
ggcgcagctg ctgttcttgc agtttctgca cgcgccagcg cctgggcaat cggcattcaa 540
tccgcccaaa ttaaggcgat tgaaaacgac caccactggc acgaaggcaa ctactacgaa 600
tccggctgca acccagccac cggactcggc gccgcccgac gcatcgccca cctcacctac 660
cgtggcgaac tagaaatcga cgaacgcttc ggcaccaaag cccaaaagaa cgaaaaccca 720
ctcggtccct accgcaagcc cgaccagcgc ttcgccgtgg aatcctactt ggactaccaa 780
gcagacaagc tagtacagcg tttcgacgcc ggctcctacg tcttgctcac cgacgccctc 840
aaccgccacg acattggtcg cgaccgcgga ggcctcaaca aggcactcga atccatcaaa 900
gttccagtcc ttgtcgcagg cgtagatacc gatattcggt acccctacca ccagcaagaa 960
cacctctcca gaaacctggg aaatctactg gcaatggcaa aaatcgtatc cctgtcggc 1020 cacgatgctt tcctcaccga aagccgccaa atggatcgca tcgtgaggaa cttcttcagc 1080
ctcatctccc cagacgaaga caacccttcg acctacatcg agttctacat ctaa 1134

<210> SEQ ID NO 91
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176D,L313R

<400> SEQUENCE: 91

Met Pro Thr Leu Ala Pro Ser Gly Gln Leu Glu Ile Gln Ala Ile Gly
1 5 10 15

Asp Val Ser Thr Glu Ala Gly Ala Ile Ile Thr Asn Ala Glu Ile Ala
20 25 30

Tyr His Arg Trp Gly Glu Tyr Arg Val Asp Lys Glu Gly Arg Ser Asn
35 40 45

Val Val Leu Ile Glu His Ala Leu Thr Gly Asp Ser Asn Ala Ala Asp
50 55 60

Trp Trp Ala Asp Leu Leu Gly Pro Gly Lys Ala Ile Asn Thr Asp Ile
65 70 75 80

Tyr Cys Val Ile Cys Thr Asn Val Ile Gly Gly Cys Asn Gly Ser Thr
85 90 95

Gly Pro Gly Ser Met His Pro Asp Gly Asn Phe Trp Gly Asn Arg Phe
100 105 110

Pro Ala Thr Ser Ile Arg Asp Gln Val Asn Ala Glu Lys Gln Phe Leu
115 120 125

Asp Ala Leu Gly Ile Thr Thr Val Ala Ala Val Leu Gly Gly Ser Met
130 135 140

Gly Gly Ala Arg Thr Leu Glu Trp Ala Ala Met Tyr Pro Glu Thr Val
145 150 155 160

Gly Ala Ala Ala Val Leu Ala Val Ser Ala Arg Ala Ser Ala Trp Asp
165 170 175

Ile Gly Ile Gln Ser Ala Gln Ile Lys Ala Ile Glu Asn Asp His His
180 185 190

Trp His Glu Gly Asn Tyr Tyr Glu Ser Gly Cys Asn Pro Ala Thr Gly
195 200 205

Leu Gly Ala Ala Arg Arg Ile Ala His Leu Thr Tyr Arg Gly Glu Leu
210 215 220

Glu Ile Asp Glu Arg Phe Gly Thr Lys Ala Gln Lys Asn Glu Asn Pro
225 230 235 240

Leu Gly Pro Tyr Arg Lys Pro Asp Gln Arg Phe Ala Val Glu Ser Tyr
245 250 255

Leu Asp Tyr Gln Ala Asp Lys Leu Val Gln Arg Phe Asp Ala Gly Ser
260 265 270

Tyr Val Leu Leu Thr Asp Ala Leu Asn Arg His Asp Ile Gly Arg Asp
275 280 285

Arg Gly Gly Leu Asn Lys Ala Leu Glu Ser Ile Lys Val Pro Val Leu
290 295 300

Val Ala Gly Val Asp Thr Asp Ile Arg Tyr Pro Tyr His Gln Gln Glu
305 310 315 320

His Leu Ser Arg Asn Leu Gly Asn Leu Leu Ala Met Ala Lys Ile Val
325 330 335

Ser Pro Val Gly His Asp Ala Phe Leu Thr Glu Ser Arg Gln Met Asp
340 345 350

Arg Ile Val Arg Asn Phe Phe Ser Leu Ile Ser Pro Asp Glu Asp Asn
355 360 365

Pro Ser Thr Tyr Ile Glu Phe Tyr Ile
370 375

<210> SEQ ID NO 92
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176D,L313R

<400> SEQUENCE: 92
atgcccaccc tcgcgccttc aggtcaactt gaaatccaag cgatcggtga tgtctccacc 60
gaagccggag caatcattac aaacgctgaa atcgcctatc accgctgggg tgaataccgc 120
gtagataaag aaggacgcag caatgtcgtt ctcatcgaac acgccctcac tggagattcc 180

```
aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctgggacat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

<210> SEQ ID NO 93
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176E,L313R

<400> SEQUENCE: 93

```
Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Glu
                165                 170                 175
```

```
Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375


<210> SEQ ID NO 94
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176E,L313R

<400> SEQUENCE: 94

atgcccaccc tcgcgccttc aggtcaactt gaaatccaag cgatcggtga tgtctccacc      60

gaagccggag caatcattac aaacgctgaa atcgcctatc accgctgggg tgaataccgc     120

gtagataaag aaggacgcag caatgtcgtt ctcatcgaac acgccctcac tggagattcc     180

aacgcagccg attggtgggc tgacttgctc ggtcccggca aagccatcaa cactgatatt     240

tactgcgtga tctgtaccaa cgtcatcggt ggttgcaacg gttccaccgg acctggctcc     300

atgcatccag atggaaattt ctggggtaat cgcttccccg ccacgtccat tcgtgatcag     360

gtaaacgccg aaaaacaatt cctcgacgca ctcggcatca ccacggtcgc cgcagtactt     420

ggtggttcca tgggtggtgc ccgcacccta gagtgggccg caatgtaccc agaaactgtt     480

ggcgcagctg ctgttcttgc agtttctgca cgcgccagcg cctgggagat cggcattcaa     540

tccgcccaaa ttaaggcgat tgaaaacgac caccactggc acgaaggcaa ctactacgaa     600

tccggctgca acccagccac cggactcggc gccgcccgac gcatcgccca cctcacctac     660

cgtggcgaac tagaaatcga cgaacgcttc ggcaccaaag cccaaaagaa cgaaaaccca     720

ctcggtccct accgcaagcc cgaccagcgc ttcgccgtgg aatcctactt ggactaccaa     780

gcagacaagc tagtacagcg tttcgacgcc ggctcctacg tcttgctcac cgacgccctc     840
```

```
aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

```
<210> SEQ ID NO 95
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176G,L313R

<400> SEQUENCE: 95

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gly
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
```

```
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375


<210> SEQ ID NO 96
<211> LENGTH: 1134
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Q176G,L313R

<400> SEQUENCE: 96

atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggggcat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134


<210> SEQ ID NO 97
<211> LENGTH: 377
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Q176W,L313R
```

<400> SEQUENCE: 97

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30

Tyr His Arg Trp Gly Glu Tyr Arg Val Asp Lys Glu Gly Arg Ser Asn
        35                  40                  45

Val Val Leu Ile Glu His Ala Leu Thr Gly Asp Ser Asn Ala Ala Asp
    50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Trp
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Arg Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 98
<211> LENGTH: 1134
<212> TYPE: DNA
<213> ORGANISM: Artificial Sequence -continued

```
<220> FEATURE:
<223> OTHER INFORMATION: Synthetic primer
<220> FEATURE:
<221> NAME/KEY: misc_feature
<223> OTHER INFORMATION: Q176W,L313R

<400> SEQUENCE: 98

atgcccaccc tcgcgccttc aggtcaactt gaaatccaag cgatcggtga tgtctccacc     60

gaagccggag caatcattac aaacgctgaa atcgcctatc accgctgggg tgaataccgc    120

gtagataaag aaggacgcag caatgtcgtt ctcatcgaac acgccctcac tggagattcc    180

aacgcagccg attggtgggc tgacttgctc ggtcccggca aagccatcaa cactgatatt    240

tactgcgtga tctgtaccaa cgtcatcggt ggttgcaacg gttccaccgg acctggctcc    300

atgcatccag atggaaattt ctggggtaat cgcttccccg ccacgtccat tcgtgatcag    360

gtaaacgccg aaaaacaatt cctcgacgca ctcggcatca ccacggtcgc cgcagtactt    420

ggtggttcca tgggtggtgc ccgcacccta gagtgggccg caatgtaccc agaaactgtt    480

ggcgcagctg ctgttcttgc agtttctgca cgcgccagcg cctggtggat cggcattcaa    540

tccgcccaaa ttaaggcgat tgaaaacgac caccactggc acgaaggcaa ctactacgaa    600

tccggctgca acccagccac cggactcggc gccgcccgac gcatcgccca cctcacctac    660

cgtggcgaac tagaaatcga cgaacgcttc ggcaccaaag cccaaaagaa cgaaaaccca    720

ctcggtccct accgcaagcc cgaccagcgc ttcgccgtgg aatcctactt ggactaccaa    780

gcagacaagc tagtacagcg tttcgacgcc ggctcctacg tcttgctcac cgacgccctc    840

aaccgccacg acattggtcg cgaccgcgga ggcctcaaca aggcactcga atccatcaaa    900

gttccagtcc ttgtcgcagg cgtagatacc gatattcggt acccctacca ccagcaagaa    960

cacctctcca gaaacctggg aaatctactg gcaatggcaa aaatcgtatc ccctgtcggc   1020

cacgatgctt tcctcaccga aagccgccaa atggatcgca tcgtgaggaa cttcttcagc   1080

ctcatctccc cagacgaaga caacccttcg acctacatcg agttctacat ctaa         1134
```

O-SUCCINYL HOMOSERINE TRANSFERASE MUTANT AND METHOD FOR PRODUCING O-SUCCINYL HOMOSERINE USING SAME

CROSS-REFERENCE TO RELATED APPLICATIONS

This application is the National Stage of International Application No. PCT/Krebs 2018/007409, filed on Jun. 29, 2018 claiming the priority of KR 10-2017-0083439, filed on Jun. 30, 2017, the content of each of which is incorporated by reference herein.

TECHNICAL FIELD

The present disclosure relates to an O-succinyl homoserine transferase mutant, a polynucleotide encoding the same, a microorganism including the mutant, and a method for producing O-succinyl homoserine using the microorganism.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Dec. 30, 2019, is named HANO1021US_SeqList.txt and is 127, kilobytes in size.

DEPOSIT OF BIOLOGICAL MATERIAL

The following biological materials have been deposited under the terms of the Budapest Treaty with the Korean Culture Center of Microoganisms, Yurim B/D, 45, Hongje-nae-2ga-gil, Seodaemun-gu, Seoul 120-861 Republic of Korea, and given the following number:

Deposit Accession Number Date of Deposit

*Corynebacterium glutamicum* CA05-5136 KCCM12024P May 11, 2017

*Corynebacterium glutamicum* CA05-5137 KCCM12025P May 11, 2017

The microorganisms have been deposited under conditions that assure that access to the microorganisms will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny are filed. However, it should be understood that the availability of a deposit does not constitute a license to practice the subject invention in derogation of patent rights granted by government action.

BACKGROUND ART

O-succinyl homoserine acts as a precursor of methionine, one of the essential amino acids of human body. Methionine has been used as a synthetic raw material for medical solutions and medical supplies as well as feed and food additives.

Methionine is produced by chemical or biological synthesis. Meanwhile, a two-step process of producing L-methionine by an enzyme conversion reaction from an L-methionine precursor produced by fermentation has been reported (International Publication No. WO/2008/013432).

In the two-step process, O-succinyl homoserine and O-acetyl homoserine are used as methionine precursors, and it is important to produce O-succinyl homoserine with a high yield for economical mass production of methionine.

MetA gene is a gene encoding homoserine O-succinyl transferase (MetA), as an enzyme involved in the synthesis of O-succinyl homoserine, by binding a succinyl group of succinyl-coA to homoserine. The MetA gene is one of the most important genes in development of O-succinyl homoserine-producing strains.

Strains in which O-succinyl homoserine is accumulated may be prepared by deleting metB gene that encodes cystathionine gamma synthase in a methionine biosynthesis pathway. However, O-succinyl homoserine-producing strains have a requirement for L-methionine. For this reason, the activity of homoserine O-succinyl transferase is weakened due to feedback inhibition by methionine added to a culture medium, and finally O-succinyl homoserine cannot be obtained at a high concentration.

Therefore, many of previous patents have been focused on how to free the feedback inhibition of metA from its feedback regulation system. However, homoserine O-succinyl transferase encoded by the metA gene has a low stability even as a wild-type protein, and stability thereof may further deteriorate by introducing a variation to free feedback. There is a need to remove feedback inhibition of the metA gene and improve enzymatic stability to develop stains having high O-succinyl homoserine-producing capability.

Most microorganisms in nature use O-succinyl homoserine or O-acetyl homoserine as an intermediate for biosynthesis of methionine. In general, MetA produces O-succinyl homoserine, and homoserine O-acetyltransferase (MetX) produces O-acetyl homoserine. In addition, unlike MetA, MetX is not affected by feedback inhibition and has a high enzymatic stability.

DESCRIPTION OF EMBODIMENTS

Technical Problem

As a result of intensive efforts to increase production of O-succinyl homoserine, the present inventors have found a protein having O-succinyl homoserine-synthesizing activity, thereby completing the present disclosure.

Solution to Problem

An object of the present disclosure is to provide a polypeptide having O-succinyl homoserine transferase activity and including a substitution of arginine for an amino acid at position 313 and a substitution of an amino acid other than glutamine for an amino acid at position 176 in an amino acid sequence of SEQ ID NO: 1.

Another object of the present disclosure is to provide a polynucleotide encoding the polypeptide.

Another object of the present disclosure is to provide a microorganism of the genus *Corynebacterium* producing O-succinyl homoserine and including a polypeptide having the O-succinyl homoserine transferase activity.

Another object of the present disclosure is to provide a method of producing O-succinyl homoserine including culturing the microorganism in a culture medium, and separating or recovering O-succinyl homoserine from the microorganism cultured in the culturing step or the culture medium.

Another object of the present disclosure is to provide a method of producing L-methionine including culturing the microorganism in a culture medium, and reacting the O-succinyl homoserine with a sulfide.

Advantageous Effects of Disclosure

Since the mutated O-succinyl homoserine transferase protein according to the present disclosure has an increased O-succinyl homoserine conversion activity compared to wild-type proteins, it may be used widely an effectively in mass production of O-succinyl homoserine as an alternative to conventional chemical synthesis pathways.

BEST MODE

Hereinafter, the present disclosure will be described in more detail.

Meanwhile, each description and embodiment disclosed in the present disclosure may be applied herein to describe different descriptions and embodiments. In other words, all combinations of various components disclosed in the present disclosure are included within the scope of the present disclosure. Furthermore, the scope of the present disclosure should not be limited by the detailed description provided below.

Those skilled in the art will recognize or be able to ascertain, using no more than routine experimentation, many equivalents to specific embodiments of the present disclosure. Such equivalents are intended to be encompassed in the scope of the following claims.

An aspect of the present disclosure to achieve the above objects is to provide a novel polypeptide having O-succinyl homoserine transferase activity. The novel variant polypeptide may be a polypeptide having O-succinyl homoserine transferase activity in which an amino acid at position 313 is substituted with arginine and an amino acid at position 176 is substituted with an amino acid other than glutamine in an amino acid sequence derived from *Corynebacterium glutamicum*, specifically, an amino acid sequence of SEQ ID NO: 1. In addition, the polypeptide may have the O-succinyl homoserine transferase activity and include a substitution of arginine for the amino acid at position 313 and a substitution of an amino acid other than glutamine for the amino acid at position 176 in the amino acid sequence of SEQ ID NO: 1. More specifically, the polypeptide may be a polypeptide having the O-succinyl homoserine transferase activity in which the amino acid at position 176 is substituted with asparagine, tryptophan, histidine, or glycine in the amino acid sequence of SEQ ID NO: 1, without being limited thereto.

The above-described variant polypeptide has enhanced O-succinyl homoserine transferase activity compared to that of a polypeptide of SEQ ID NO: 1 having O-succinyl homoserine transferase activity.

As used herein, the term "O-succinyl homoserine transferase activity" refers to activity that converts homoserine into O-succinyl homoserine. The O-succinyl homoserine transferase is a generic name of enzymes capable of converting succinyl CoA and L-homoserine, as substrates, into CoA and O-succinyl homoserine.

[Reaction Scheme]

Succinyl CoA+L-homoserine⇔CoA+O-succinyl homoserine

In the present disclosure, O-succinyl homoserine transferase refers to a modified MetX protein that is O-acetyl homoserine transferase via modification of a part of an amino acid sequence thereof with other amino acids, thereby having the activity of O-succinyl homoserine transferase. The MetX protein may be MetX derived from the genus *Corynebacterium*, more specifically MetX having an amino acid sequence of SEQ ID NO: 1 derived from *Corynebacterium glutamicum*, but is not limited thereto. The MetX protein may be obtained from known GenBank database of The National Center for Biotechnology Information (NCBI).

In the present disclosure, O-succinyl homoserine transferase may be obtained by various methods well known in the art. Examples of the methods include a gene synthesis technique including codon optimization such that an enzyme is obtained with a high yield in a microorganism of the genus *Corynebacterium* that has been widely used in expression of enzymes and a method of screening useful enzyme resources using a bioinformatic method based on a large amount of genome information of microorganisms, but are not limited thereto.

In the present disclosure, the term "O-succinyl homoserine transferase mutant" may be interchangeably used with the terms "mutated O-succinyl homoserine transferase" or "variant O-succinyl homoserine transferase". Meanwhile, this mutant may be a non-naturally occurring mutant.

Specifically, the mutated O-succinyl homoserine transferase according to the present disclosure may include an amino acid sequence in which a $313^{th}$ amino acid residue from the N-terminal of MetX derived from *Corynebacterium* sp. having an amino acid sequence of SEQ ID NO: 1 is substituted with arginine and a $176^{th}$ amino acid thereof is substituted with an amino acid other than glutamine. Specifically, the $176^{th}$ glutamine amino acid residue may be substituted with asparagine, tryptophan, histidine, or glycine, without being limited thereto. The mutated O-succinyl homoserine transferase according to the present disclosure may include a polypeptide having a variation at position 313 and/or position 176 from the N-terminal of the amino acid sequence set forth in SEQ ID NO: 1, wherein the variation at position 313 includes an amino acid substitution with arginine and/or the variation at position 176 includes an amino acid substitution with asparagine, tryptophan, histidine, or glycine, and the polypeptide has a homology or identity of at least 85% with SEQ ID NO: 1, without being limited thereto.

In addition, the polypeptide having the O-succinyl homoserine transferase activity according to the present disclosure may consist of at least one amino acid sequence selected from the group consisting of amino acid sequences of SEQ ID NOS: 63, 75, 95, and 97. Specifically, these amino acid sequences may be amino acid sequences of polypeptides having mutated O-succinyl homoserine transferase activity in which the $313^{th}$ amino acid from the N-terminal of the amino acid sequence of SEQ ID NO: 1 is substituted with arginine, and the $176^{th}$ amino acid thereof is substituted with asparagine, tryptophan, histidine, or glycine, but the present disclosure is not limited thereto. Any polypeptides having a homology or identify of at least 50%, 60%, 70%, 75%, 80%, 85%, 90%, 95%, 97%, or 99% with the sequences described above may be used without limitation so long as the polypeptides have the variations and better O-succinyl homoserine conversion activity than the wild-type.

Also, MetX of the present disclosure may be a MetX protein having the amino acid sequence of SEQ ID NO: 1 or an amino acid sequence having a homology or identify of at least 80% therewith, but is not limited thereto. Specifically, the MetX protein according to the present disclosure may include proteins having the amino acid sequence of SEQ ID NO: 1 and an amino acid sequence having a homology or identify of 80% or more, 85% or more, specifically 90% or more, more specifically 95% or more, even more specifically 99% or more with SEQ ID NO: 1.

As used herein, the term a "variant" of a polypeptide refers to a polypeptide having an amino acid sequence different from the recited sequence by conservative substitutions and/or modifications such that functions and properties of the polypeptide are retained. Variant polypeptides differ from a sequence identified by substitution, deletion, or addition of several amino acids. Such variants may generally be identified by modifying one of the above polypeptide sequences and evaluating properties of the modified polypeptide. That is, the ability of the variant may be enhanced, unchanged, or diminished relative to a native protein. Such variants may generally be identified by modifying one of the above polypeptide sequences and evaluating the reactivity of the modified polypeptide. In addition, some variants may include those in which one or more portions, such as an N-terminal leader sequence or transmembrane domain, have been removed. Other variants may include those in which a portion has been removed from the N- and/or C-terminal of a mature protein. The term "variant" may be interchangeably used with terms such as mutant, modification, mutated protein, variant polypeptide, modified protein, modified polypeptide, mutein, divergent, and the like, without limitation, as long as the terms are used to indicate variation. Specifically, the variant includes variants having an effectively enhanced activity of O-succinyl homoserine transferase compared to wild-type by variation of amino acids of O-succinyl homoserine transferase derived from *Corynebacterium glutamicum.*

As used herein, the term "conservative substitution" refers to one amino acid substituted with another amino acid having a similar structural and/or chemical property. For example, the variant may have at least one conservative substitution while retaining at least one biological activity. Such amino acid substitution may generally occur based on similarity of polarity, charge, solubility, hydrophobicity, hydrophilicity, and/or amphipathic nature of a residue. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan. In general, conservative substitution has little or no influence on the activity of a produced polypeptide.

Variants may also include other modifications including deletion or addition of amino acids that have minimal influence on properties and a secondary structure of the polypeptide. For example, the polypeptide may be conjugated to a signal (or leader) sequence at the N-terminal of a protein which co-translationally or post-translationally directs transfer of the protein. The polypeptide may also be conjugated with another sequence or linker to identify, purify, or synthesize the polypeptide. In other words, although it is disclosed as 'a protein or polypeptide having an amino acid sequence set forth in a given SEQ ID NO:', it will be obvious to those skilled in the art that any protein having an amino acid sequence including a deletion, a modification, a substitution, a conservative substitution, or an addition of one or several amino acids may also be used in the present disclosure as long as the protein has homologous or identical activity to that of the polypeptide having the same SEQ ID NO: For example, it is obvious to those skilled in the art that any protein having an addition of a sequence not changing functions of the protein, a naturally occurring mutation or a silent mutation thereof, or a conservative substitution in the forward or reverse direction is not excluded as long as the protein has homologous or identical activity to with that of the variant polypeptide, and any protein having such addition of a sequence or mutation may also be within the scope of the present disclosure.

Also, it is obvious that the polynucleotide that is translated into the protein comprising at least one amino acid sequence selected from the group consisting of amino acid sequences of SEQ ID NOS: 63, 75, 95, and 97 or proteins having a homology or identity therewith by codon degeneracy may also be used. Or, any probe prepared from known gene sequences, e.g., a sequence which are hybridized, under stringent conditions, with a sequence totally or partially complementary to a polynucleotide sequence and encodes the protein having the O-succinyl homoserine transferase activity may also be used, without limitation. The term "stringent conditions" refers to conditions which permit specific hybridization between polynucleotides. Such conditions are disclosed in detail in known documents (e.g., J. Sambrook et al., supra, 9.50-9.51, 11.7-11.8). For example, the stringent conditions may include performing hybridization between genes having a high homology or identity, a homology or identity of 80% or more, 85% or more, specifically 90% or more, more specifically 95% or more, even more specifically 97% or more, and most specifically 99% or more, without performing hybridization between genes having a homolog or identity lower than the above homologies or identities, or performing washing once, specifically twice or three times, under conventional washing conditions for Southern hybridization of 60° C., 1×SSC, and 0.1% SDS, specifically at a salt concentration and a temperature of 60° C., 0.1×SSC, and 0.1% SDS, and more specifically 68° C., 0.1×SSC, and 0.1% SDS.

Hybridization requires that two nucleic acids have complementary sequences, although mismatch between bases according to the degree of stringency of hybridization is possible. The term "complementary" is used to describe the relationship between nucleotide bases capable of hybridizing with each other. For example, with respect to DNA, adenosine is complementary to thymine, and cytosine is complementary to guanine. Thus, the present disclosure may include not only a substantially similar nucleic acid sequence but also a nucleic acid fragment isolated but complementary to the entire sequence.

Specifically, the polynucleotide having homology or identity may be detected using the above-described hybridization conditions including a hybridization process at a Tm value of 55° C. Also, the Tm value may be, but is not limited to, 60° C., 63° C., or 65° C. and may be appropriately adjusted by those skilled in the art according to the purpose.

An appropriate degree of stringency for hybridization of polynucleotides may depend on lengths of the polynucleotides and a degree of complementarity and parameters thereof are well known in the art (Sambrook et al., supra, 9.50-9.51, 11.7-11.8).

The homology or identity refers to a degree of relevance between two amino acid sequences or nucleotide sequences and may be expressed as a percentage.

The terms homology and identity may often be used interchangeably.

Sequence homology or identity of conserved polynucleotides or polypeptides may be determined by standard alignment algorithm and default gap penalties established by a used program may be used together therewith. Substantially, homologous or identical sequences may hybridize to each other along at least about 50%, 60%, 70%, 80%, or 90% of the entire sequence or the entire length under moderate or highly stringent conditions. In hybridized polynucleotides, polynucleotides including degenerated codon instead of codon may also be considered.

Whether any two polynucleotides or polypeptide sequences have homology, similarity, or identity may be determined using computer algorithms known in the art, e.g., "FASTA" program using default parameters introduced by Pearson et al (1988) [Proc. Natl. Acad. Sci. USA 85]: 2444. Alternatively, Needleman-Wunsch algorithm (1970, J. Mol. Biol. 48: 443-453) performed in a Needleman program of The European Molecular Biology Open Software Suite (EMBOSS) package (Rice et al., 2000, Trends Genet. 16: 276-277) (version 5.0.0 or later) may be used to determine the same (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, the homology, similarity, or identity may be determined using BLAST, from the National Center for Biotechnology Information database, or ClustalW.

The homology, similarity, or identity between polynucleotides or polypeptides may be determined by comparing sequence information using a GAP computer program, such as a program introduced by Needleman et al., (1970), J Mol Biol. 48: 443 as disclosed in Smith and Waterman, Adv. Appl. Math (1981) 2:482. In brief, the GAP program defines homology, similarity, or identity as the number of aligned symbols (i.e., nucleotides or amino acids) which are similar, divided by the total number of symbols in a shorter of two sequences. Default parameters for the GAP program may include: (1) a unary comparison matrix (containing a value of 1 for identities and 0 for non-identifies) and the weighted comparison matrix of Gribskov, et al., (1986) Nucl. Acids Res. 14: 6745 as described by Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps. Thus, as used herein, the term "homology" or "identity" refers to relevance between sequences.

Another aspect of the present disclosure is to provide a polynucleotide encoding the polypeptide having the O-succinyl homoserine transferase activity.

As used herein, the term "polynucleotide" refers to a polymer of nucleotides, wherein nucleotide monomers are connected in a long chain-like manner by covalent bonds, generally indicating a DNA or RNA strand having a certain minimum length, more specifically a polynucleotide fragment encoding the variant polypeptide.

In the present disclosure, a gene encoding the amino acid sequence of O-succinyl homoserine transferase is a variant O-succinyl homoserine transferase gene, specifically derived from *Corynebacterium glutamicum*. Based on genetic code degeneracy, a nucleotide sequence encoding the same amino acid sequence and mutants thereof are also included in the present disclosure, and examples thereof may be set forth in SEQ ID NOs: 64, 76, 96, or 98, without being limited thereto.

In addition, in the case of the variant polynucleotide, a nucleotide sequence encoding the same amino acid sequence and mutants thereof are also included in the present disclosure based on genetic code degeneracy.

Another aspect of the present disclosure is to provide a host cell including a polynucleotide encoding the variant polypeptide and a microorganism transformed by the vector including a polynucleotide encoding the variant polypeptide. Specifically, the introduction may be performed by transformation, but is not limited thereto.

Specifically, since a microorganism including a variant O-succinyl homoserine transferase polypeptide has enhanced O-succinyl homoserine-producing capability without inhibiting the growth of the host cell when compared with a microorganism including a wild-type O-succinyl homoserine transferase polypeptide, O-succinyl homoserine may be obtained from these microorganisms with a high yield.

As used herein, the term "vector" refers to a DNA construct containing the nucleotide sequence of a target protein-encoding polynucleotide operably linked to a suitable regulatory sequence so as to be able to express the target protein in a suitable host cell. The regulatory sequence may include a promoter capable of initiating transcription, any operator sequence for regulating the transcription, a sequence encoding a suitable mRNA ribosome binding site, and a sequence for regulating termination of transcription and translation. Once transformed into a suitable host cell, the vector may replicate or function independently from the host genome, or may integrate into genome thereof.

The vector used in the present disclosure is not particularly limited as long as it may replicate in a host and may be any vector known in the art. Examples of the commonly used vectors may include natural or recombinant plasmids, cosmids, viruses, and bacteriophages. For example, pWE15, M13, MBL3, MBL4, IXII, ASHII, APII, t10, t11, Charon4A, and Charon21A may be used as a phage vector or cosmid vector, and pBR-based, pUC-based, pBluescriptII-based, pGEM-based, pTZ-based, pCL-based, and pET-based vectors may be used as a plasmid vector. Specifically, pDZ, pACYC177, pACYC184, pCL, pECCG117, pUC19, pBR322, pMW118, and pCC1BAC vectors may be used, without being limited thereto.

Vectors available in the present disclosure are not particularly limited and any known expression vectors may be used. In addition, a polynucleotide encoding a target protein may be inserted into a chromosome using a vector for chromosomal insertion into cells. The insertion of the polynucleotide into the chromosome may be performed by any method known in the art, for example, homologous recombination, without being limited thereto. The polynucleotide may further include a selection marker to confirm chromosomal insertion. The selection marker is used to select cells that are transformed by the vector, that is, to confirm insertion of a desired nucleic acid molecule, and the selection marker may include markers providing selectable phenotypes, such as drug resistance, nutrient requirement, resistance to cytotoxic agents, or surface protein expression. Only cells expressing the selection marker are able to survive or to show different phenotypes under the environment treated with the selective agent, and thus the transformed cells may be selected.

As used herein, the term "transformation" means the introduction of a vector including a polynucleotide encoding a target protein into a host cell in such a way that the protein encoded by the polynucleotide is expressed in the host cell. As long as the transformed polynucleotide may be expressed in the host cell, it may be inserted into and located in the chromosome of the host cell or exist extrachromosomally. In addition, the polynucleotide includes DNA and RNA encoding the target protein. The polynucleotide may be introduced in any form, as long as it is able to be introduced into the host cell and expressed therein. For example, the polynucleotide may be introduced into the host cell in the form of an expression cassette, which is a gene construct including all elements required for autonomous expression thereof. Typically, the expression cassette includes a promoter operably linked to the polynucleotide, a transcriptional termination signal, a ribosome binding site, and a translation termination signal. The expression cassette may be in the form of a self-replicable expression vector. Also, the polynucleotide as it is may be introduced into the host cell and operably linked to a sequence required for expression in the host cell, without being limited thereto. Methods for transformation include any methods for introducing a nucleic acid into cells, and may be performed by suitable standard techniques known in the art. For instance, transformation methods may include electroporation, calcium phosphate ($Ca(H_2PO_4)_2$, $CaHPO_4$, or $Ca_3(PO_4)_2$) precipitation, calcium chloride ($CaCl_2$) precipitation, microinjection, polyethylene glycol (PEG) method, DEAE-dextran method, cationic liposome method, and Lithium acetate dihydrate-DMSO method, without being limited thereto.

In addition, as used herein, the term "operably linked" means a functional linkage between a promoter sequence which initiates and mediates transcription of the polynucleotide encoding the target protein of the present disclosure and the polynucleotide sequence. An operable linkage may be performed by a genetic recombination technique known in the art, and site-specific DNA cleavage and ligation may be performed using a restriction enzyme, a ligase, and the like, known in the art, without being limited thereto.

As used herein, the "microorganism producing O-succinyl homoserine" refers a microorganism naturally having O-succinyl homoserine-producing capability or a microorganism prepared by providing the O-succinyl homoserine-producing capability to a parent strain unable to produce O-succinyl homoserine.

The microorganism producing O-succinyl homoserine may be a cell or microorganism including a polynucleotide encoding a variant polypeptide or a cell or microorganism transformed by a vector including a polynucleotide encoding the variant polypeptide to have the ability to express the variant polypeptide. For the purpose of the present disclosure, the host cell or microorganism may be any microorganisms capable of producing O-succinyl homoserine by including a variant MetX polypeptide. Examples of the microorganism may include microorganisms belonging to the genus Escherichia, the genus Serratia, the genus *Erwinia*, the genus *Enterobacteria*, the genus *Salmonella*, the genus *Streptomyces*, the genus *Pseudomonas*, the genus *Brevibacterium*, or the genus *Corynebacterium*, specifically microorganisms of the genus *Corynebacterium*, and more specifically *Corynebacterium glutamicum*, without being limited thereto.

As used herein, the term "a microorganism of the genus *Corynebacterium* producing O-succinyl homoserine" refers to a microorganism belonging to the genus *Corynebacterium* naturally having O-succinyl homoserine-producing capability or having the same by mutation. It is well known in the art that cultures of the microorganism of the genus *Corynebacterium* contain O-succinyl homoserine. However, the O-succinyl homoserine-producing capability is considerably low and a gene or mechanism affecting a production mechanism thereof has not been discovered yet. Thus, the microorganism of the genus *Corynebacterium* having the O-succinyl homoserine-producing capability according to the present disclosure refers to a wild-type microorganism of the genus *Corynebacterium*, a microorganism of the genus *Corynebacterium* into which an external gene related to the O-succinyl homoserine-producing mechanism is inserted or a microorganism of the genus *Corynebacterium* modified to have enhanced O-succinyl homoserine-producing capability by enhancing intrinsic activity of the gene or inactivating it.

In the present disclosure, the term "microorganism of the genus *Corynebacterium*" refers specifically to *Corynebacterium glutamicum, Corynebacterium ammoniagenes, Brevibacterium lactofermentum, Brevibacterium flavum, Corynebacterium thermoaminogenes, Corynebacterium efficiens*, or the like, without being limited thereto. More specifically, the microorganism of the genus *Corynebacterium* according to the present disclosure may be *Corynebacterium glutamicum*, the growth and survival of which are less affected even when exposed to a high concentration of O-succinyl homoserine.

In the microorganism, at least one protein selected from the group consisting of cystathionine synthase, O-acetyl homoserine (thiol)-lyase, and homoserine kinase may be inactivated. That is, one, two, or three proteins selected therefrom may be inactivated.

As used herein, the term "inactivation" of a protein activity means that the activity of the protein is weakened compared to the intrinsic activity or the protein has no activity.

The inactivation of the protein activity may be achieved by various methods well known in the art. Examples of the methods may include: a method of deleting a part or the entirety of a gene encoding the protein on the chromosome including removing the activity of the protein; a method of replacing the gene encoding the protein on the chromosome with a mutated gene to reduce the enzymatic activity; a method of introducing a variation into an expression regulatory sequence of a gene encoding the protein on the chromosome; a method of replacing the expression regulatory sequence of the gene encoding the protein with a sequence having a weak activity or no activity (e.g., a method of replacing a promoter of the gene with a promoter weaker than an endogenous promoter); a method of deleting a part or the entirety of the gene encoding the protein on the chromosome; a method of introducing an antisense oligonucleotide (e.g., antisense RNA), which inhibits translation from an mRNA into the protein via a complementary binding to a transcript of the gene on the chromosome; a method of making the attachment of a ribosome impossible by forming a secondary structure by artificially adding a complementary sequence to the Shine-Dalgarno (SD) sequence on the frontend of the SD sequence of the gene encoding the protein; and a reverse transcription engineering (RTE) method, which adds a promoter for reverse transcription to the 3' terminal of the open reading frame (ORF) of the corresponding sequence, and a combination thereof, but are not particularly limited thereto.

Specifically, the method of deleting a part or the entirety of the gene encoding the protein may be executed by replacing the polynucleotide encoding the endogenous target protein within the chromosome with a polynucleotide or a marker gene having a partially deleted nucleic acid sequence using a vector for chromosomal insertion into microorganisms. For example, a method of deleting a gene by homologous recombination may be used, without being limited thereto. Also, as used herein, the term "part" may specifically refer to 1 nucleotide to 300 nucleotides, more specifically 1 nucleotide to 100 nucleotides, and even more specifically 1 nucleotide to 50 nucleotides although it may vary depending on the kinds of polynucleotide, and those skilled in the art may decide it appropriately. However, the part is not particularly limited thereto.

Additionally, the method of modifying the expression regulatory sequence may be performed by inducing a variation of nucleic acid sequence in the expression regulatory sequence via deletion, insertion, conservative substitution, non-conservative substitution, or any combination thereof so as to further weaken the activity of the expression regulatory sequence; or by replacing the sequence with a nucleic acid sequence having a weaker activity. The expression regulatory sequence may include a promoter, an operator sequence, a sequence encoding a ribosome-binding site, and a sequence for regulating transcription and translation, but is not limited thereto.

In addition, the method of modifying the gene sequence on the chromosome may be performed by inducing a variation in the gene sequence via deletion, insertion, conservative substitution, non-conservative substitution, or any combination thereof so as to further weaken the activity of the protein; or by replacing the sequence with a gene sequence modified to have a weaker activity or a gene sequence modified to have no activity at all, but is not limited thereto. Specifically, in the microorganism, at least one gene selected from the group consisting of metB gene encoding cystathionine gamma synthase, metY gene encoding O-acetyl homoserine (thiol)-lyase used in a degradation pathway of O-succinyl homoserine, and gene thrB encoding homoserine kinase may further be deleted or weakened.

As used herein, the term "deletion" refers to a type of removal, within the chromosome, of a nucleotide sequence corresponding to from a start codon to a stop codon of a target gene, or a part or the entirety of a nucleotide sequence of a regulatory region thereof.

As used herein, the term "weakening" refers to removal or reduction of intracellular activity of at least one enzyme encoded by a corresponding DNA in a microorganism strain. For example, expression of a protein may be weakened by modifying a promoter region and a nucleotide sequence of 5'-UTR region, or the activity of the protein may be weakened by introducing a mutation into the ORF region of the corresponding gene. Specifically, in the microorganism, at least one gene selected from the group consisting of metB gene encoding cystathionine gamma synthase, metY gene encoding O-acetyl homoserine (thiol)-lyase in the degradation pathway of O-succinyl homoserine, and gene thrB encoding homoserine kinase may further be deleted or weakened.

In addition, the microorganism of the genus *Corynebacterium* may be a microorganism of the genus *Corynebacterium* producing O-succinyl homoserine with enhanced aspartokinase activity compared to non-mutated microorganisms.

As used herein, the term "enhancement" of protein activity means that the activity of the protein is introduced or increased compared to intrinsic activity thereof. The "introduction" of the activity means that a microorganism acquires activity of a particular polypeptide which has not been naturally or artificially possessed by the microorganism.

As used herein, the term "increase" in the activity of the protein relative to the intrinsic activity means that the activity of the protein included in the microorganism is enhanced compared to the intrinsic activity of the protein or the activity before modification. The term "intrinsic activity" refers to activity of a particular protein originally possessed by a parent strain or non-modified microorganism before transformation when the microorganism is transformed by genetic variation caused by a natural or artificial factor. The intrinsic activity may also be interchangeably used with activity before modification.

Specifically, the increase in activity according to the present disclosure may be achieved by one of the following methods:

(1) a method of increasing copy number of a polynucleotide encoding the protein, (2) a method of modifying an expression regulatory sequence to increase expression of the polynucleotide, (3) a method of modifying a polynucleotide sequence on a chromosome to enhance the activity of the protein, (4) a method of introducing a foreign polynucleotide having the activity of the protein or a codon optimized variant polynucleotide of the polynucleotide, or (5) a method of enhancing the activity by any combination thereof, but the methods are not limited thereto.

The increase in the copy number of polynucleotide described in (1) above is not particularly limited, but may be performed in a form operably linked to a vector or in an integrated form into a chromosome of a host cell. Specifically, this method may be performed by introducing a vector, which may replicate and function irrespective of a host, operably linked to a polynucleotide encoding the protein of the present disclosure, into a host cell; or by introducing a vector, which may insert the polynucleotide into the chromosome of the host cell, operably linked to the polynucleotide into a host cell, thereby increasing the copy number of the polynucleotide in the chromosome of the host cell.

Next, the modification of the expression regulatory sequence to increase the expression of the polynucleotide described in (2) above may be performed by inducing a variation in the nucleic acid sequence by deletion, insertion, conservative substitution, non-conservative substitution, or any combination thereof to further enhance the activity of the expression regulatory sequence, or by replacing with a nucleic acid sequence having a stronger activity, without being limited thereto. The expression regulatory sequence may include a promoter, an operator sequence, a sequence encoding a ribosome-binding site, and a sequence for regulating of termination of transcription and translation, without being limited thereto.

A strong heterologous promoter instead of the original promoter may be linked upstream of the polynucleotide expression unit, and examples of the strong promoter may include a CJ7 promoter (Korean Patent No. 0620092 and International Publication No. WO2006/065095), a lysCP1 promoter (International Publication No. WO2009/096689), an EF-Tu promoter, a groEL promoter, or an aceA, or aceB promoter, without being limited thereto. In addition, the modification of the polynucleotide sequence on the chromosome described in (3) above, may be performed by inducing a variation in the expression regulatory sequence by deletion, insertion, conservative substitution, non-conservative substitution, or any combination thereof to further enhance the activity of the polynucleotide sequence, or by replacing with a polynucleotide sequence modified to having a stronger activity, without being limited thereto.

In addition, the introduction of the foreign polynucleotide sequence described in (4) above may be performed by introducing a foreign polynucleotide encoding a protein having activity identical/similar to that of the protein, or a codon optimized variant polynucleotide thereto into the host cell. The foreign polynucleotide may be any polynucleotides having activity identical/similar to that of the protein without limitation. In addition, an optimized codon thereof may be introduced into the host cell to perform optimized transcription and translation of the introduced foreign polynucleotide in the host cell. The introduction may be performed by any known transformation method suitably selected by those of ordinary skill in the art. When the introduced polynucleotide is expressed in the host cell, the protein is produced and the activity thereof may be increased.

Finally, the method of enhancing the activity by any combination of the methods (1) to (4) described in (5) above may be performed by combining at least one of the methods of increasing the copy number of polynucleotide encoding the protein, modifying the expression regulatory sequence to increase expression thereof, modifying the polynucleotide sequence on the chromosome, and modifying the foreign polynucleotide having the activity of the protein or a codon optimized variant polynucleotide thereof.

In the present disclosure, the sequences of the genes or polynucleotides above may be obtained from database of The National Center for Biotechnology Information (NCBI), and the like.

Another aspect of the present disclosure is to provide a method of producing O-succinyl homoserine, the method including culturing the above-described microorganism, and recovering O-succinyl homoserine from the cultured microorganism or a culture medium.

Another aspect of the present disclosure is to provide a method of producing L-methionine, the method including culturing the above-described microorganism, and reacting the cultured microorganism or O-succinyl homoserine with a sulfide.

Specifically, the reaction with the sulfide refers to a process of generating L-methionine from O-succinyl homoserine using any known method. For example, L-methionine may be produced by reacting O-succinyl homoserine with methyl mercaptan, as a sulfide, or by a step-like reaction after producing cystathionine via reaction with cysteine, as a sulfide. In addition, a catalyst or an enzyme may be added or reaction may be performed in a microorganism including an enzyme to improve reaction rates and yields.

The 'O-succinyl homoserine' may be a fermentation liquid or purified form containing O-succinyl homoserine produced by the microorganism according to the present disclosure. In addition, the 'sulfide' may be, for example, methyl mercaptan, and the methyl mercaptan may mean any methyl mercaptan derivatives capable of providing sulfur atoms such as dimethylsulfide (DMS) disclosed in International Publication No. WO2010/098629 as well as sodium methyl mercaptan ($CH_3S$—Na) in a liquid phase and methyl mercaptan ($CH_3SH$) in a gaseous or liquid state.

The method of producing L-methionine may be easily determined by those of ordinary skill in the art based on optimized culture conditions and enzymatic activity conditions well known in the art. Detailed descriptions of the culturing method and culture medium are given above.

In addition, the method of producing L-methionine may further include separating or recovering O-succinyl homoserine from the microorganism cultured in the culturing process or the medium.

It will be obvious that the "O-succinyl homoserine" of the present disclosure may include salt forms of O-succinyl homoserine as well as O-succinyl homoserine itself.

In the method, the step of culturing the microorganism may be performed by, but is not limited to, batch culture, continuous culture, and fed-batch culture known in the art. In this regard, the culture conditions are not particularly limited, but an optimal pH (e.g., pH 5 to 9, preferably pH 6 to 8, and most preferably pH 6.8) may be adjusted by using a basic compound (e.g., sodium hydroxide, potassium hydroxide, or ammonia) or an acidic compound (e.g., phosphoric acid or sulfuric acid). Also, an aerobic condition may be maintained by adding oxygen or an oxygen-containing gas mixture to a cell culture. The culture temperature may be maintained at 20° C. to 45° C., and preferably 25° C. to 40° C., and the cultivation may be performed for about 10 hours to 160 hours, without being limited thereto. O-succinyl homoserine produced during the cultivation may be exported into the medium or remain in the cells.

Examples of a carbon source to be contained in the culture medium may include saccharides and carbohydrates (e.g., glucose, sucrose, lactose, fructose, maltose, molasse, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), and organic acids (e.g., acetic acid). These carbon sources may be used alone or in combination, but are not limited thereto. Examples of a nitrogen source may include a nitrogen-containing organic compound (e.g., peptone, yeast extract, meat gravy, malt extract, corn steep liquor, bean flour, and urea), and an inorganic compound (e.g., ammonium sulfate, ammonium chloride, ammonium phosphate, ammonium carbonate, and ammonium nitrate). These nitrogen sources may be used alone or in combination, but are not limited thereto. As a phosphorous source, potassium dihydrogen phosphate, dipotassium hydrogen phosphate, and sodium-containing salts corresponding thereto may be used alone or in combination without being limited thereto. In addition, the medium may include essential growth-promoting materials such as a metal salt (e.g., magnesium sulfate or iron sulfate), amino acids, and vitamins.

The O-succinyl homoserine or L-methionine produced in the culturing step in the present disclosure may be recovered from the culture media using any known method of collecting desired amino acids suitably selected according to the culturing method. For example, centrifugation, filtration, anion exchange chromatograph, crystallization, and HPLC may be used, and desired O-succinyl homoserine or L-methionine may be recovered from the media or microorganism using any suitable method well known in the art.

MODE OF DISCLOSURE

Hereinafter, the present disclosure will be described in more detail with reference to the following examples. However, these examples are for illustrative purposes only and are not intended to limit the scope of the present disclosure.

Example 1: Preparation of metX Plasmid Having O-Acetyl Homoserine Transferase Activity In order to amplify a gene encoding O-acetyl homoserine transferase (MetX), a BamHI restriction enzyme site was inserted into both ends of each of primers (SEQ ID NOs: 5 and 6) for amplification from a promoter region (located about 300 bp upstream from a start codon) to a terminator region (located about 100 bp downstream from a stop codon) based on a reported sequence derived from a wild-type (WT).

TABLE 1

| SEQ ID NO: | Primer | Sequence (5'-3') |
|---|---|---|
| 5 | Primer 1 | GGATCCCCTCGTTGTTCACCCAGCAACC |
| 6 | Primer 2 | GGATCCCAAAGTCACAACTACTTATGTTAG |

PCR was performed under the following conditions. After denaturation at 95° C. for 5 minutes, cycles of denaturation at 95° C. for 30 seconds, annealing at 55° C. for 30 seconds, and polymerization at 72° C. for 90 seconds were repeated 30 times, and then polymerization was performed at 72° C.

for 7 minutes. As a result, a DNA fragment of 1546 bp was obtained as a coding region of a metX gene. A pECCG117 vector (Korean Patent No. 10-0057684) and the metX DNA fragment were treated with a restriction enzyme BamHI, ligated using a DNA ligase, and cloned to obtain a plamid which was named pECCG117-metX WT.

Example 2: Preparation of Variant metX Plasmid having O-succinyl Homoserine Transferase Activity New metX mutation sites were selected, and amino acids at position 176 and 313 of the amino acid sequence of SEQ ID NO: 1 were substituted with another amino acid, respectively.

More specifically, Q176N and L313R mutation was performed. A primer pair for mutation at position 176 (SEQ ID NOs: 7 and 8) and a primer pair for mutation at position 313 (SEQ ID NOS: 9 and 10) were designed to prepare a mutation vector to substitute the $176^{th}$ amino acid of O-acetyl homoserine transferase with another amino acid and substitute the $313^{th}$ amino acid thereof with arginine using the pECCG117-metXWT plasmid prepared in Example 1 as a template.

TABLE 2

| SEQ ID NO: | Primer | Sequence (5'-3') |
|---|---|---|
| 7 | Primer 3 | ACGCGCCAGCGCCTGGAACATCGGCATTCAATCCG |
| 8 | Primer 4 | CGGATTGAATGCCGATGTTCCAGGCGCTGGCGCGT |
| 9 | Primer 5 | GTAGATACCGATATTCGGTACCCCTACCACCAG |
| 10 | Primer 6 | CTGGTGGTAGGGGTACCGAATATCGGTATCTAC |

A mutated metX gene was prepared using the primers and a site-directed mutagenesis kit (Stratagene, USA). Mutated L313R plasmid based on the existing wild-type (WT) plasmid was named WT_L313R, and mutated Q176N and L313R plasmid was named WT_Q176N_L313R.

Example 3: Comparison Test of Substrate Specificity and Activity of Variant metX having O-succinyl Homoserine Transferase Activity For comparisons of activities of mutated metX that produce excessive amounts of O-succinyl homoserine, strains in which homoserine is accumulated and utilization of produced O-succinyl homoserine was deleted were prepared. Prepared were strains in which a metB gene encoding cystathionine gamma synthase in a degradation pathway of O-succinyl homoserine was deleted and a metY gene encoding O-acetyl homoserine (thiol)-lyase in a degradation pathway of O-succinyl homoserine was deleted. First, for deletion of the metB gene, a primer pair (SEQ ID NOs: 11 and 12) for amplification of 5' upstream region of the metB gene and a primer pair (SEQ ID NOs: 13 and 14) for amplification of 3' downstream region of the metB gene were designed based on nucleotide sequence information of the WT-derived metB gene. An XbaI restriction enzyme site (underlined) was inserted to ends of each of the primers of SEQ ID NOs: 11 and 14.

TABLE 3

| SEQ ID NO: | Primer | Sequence (5'-3') |
|---|---|---|
| 11 | Primer 7 | TCTAGATGCGCTGATTATCTCACC |
| 12 | Primer 8 | ACTGGTGGGTCATGGTTGCATATGAGATCAACTCCTGTAA |
| 13 | Primer 9 | TTACAGGAGTTGATCTCATATGCAACCATGACCCACCAGT |
| 14 | Primer 10 | TCTAGACCTTGAAGTTCTTGACTG |

PCR was performed using a WT chromosome as a template and using the primers of SEQ ID NOs: 11 and 12 and SEQ ID NOs: 13 and 14. PCR was performed under the following conditions. After denaturation at 95° C. for 5 minutes, cycles of denaturation at 95° C. for 30 seconds, annealing at 55° C. for 30 seconds, and polymerization at 72° C. for 90 seconds were repeated 30 times, and then polymerization was performed at 72° C. for 7 minutes. As a result, a DNA fragment of 450 bp of 5' upstream region of the metB gene and a DNA fragment of 467 bp of 3' downstream region of the metB gene were obtained.

PCR was performed using the two amplified DNA fragments as templates and the primers of SEQ ID NOs: 11 and 14. PCR was performed under the following conditions. After denaturation at 95° C. for 5 minutes, cycles of denaturation at 95° C. for 30 seconds, annealing at 55° C. for 30 seconds, and polymerization at 72° C. for 3 minutes were repeated 30 times, and then polymerization was performed at 72° C. for 7 minutes. As a result, a DNA fragment of 917 bp including only upstream and downstream ends of the metB gene with a deleted central region thereof was amplified.

A pDZ vector and the DNA fragment of 917 bp were treated with the restriction enzyme XbaI, ligated using a DNA ligase, and cloned to obtain a plasmid which was named pDZ-ΔmetB.

The pDZ-ΔmetB vector was introduced into WT strains by an electric-pulse method and transformed strains were obtained from a medium for selection including 25 mg/L of kanamycin. The selected strains were subjected to a secondary recombination process of cross-over to obtain the WT ΔmetB strain in which the metB gene was deleted by the DNA fragment inserted into the chromosome.

For deletion of the metY gene in another degradation pathway of O-succinyl homoserine, a primer pair (SEQ ID NOs: 15 and 16) for amplification of 5' upstream region of the metY gene and a primer pair (SEQ ID NOs: 17 and 18) for amplification of 3' downstream region of the metY gene were designed based on nucleotide sequence information of WT-derived metY gene. An XbaI restriction enzyme site (underlined) was inserted into ends of each of the primers of SEQ ID NOs: 15 and 18.

TABLE 4

| SEQ ID NO: | Primer | Sequence (5'-3') |
|---|---|---|
| 15 | Primer 11 | TCTAGAAGTAGCGTTGCTGTACAC |
| 16 | Primer 12 | ATCAATGGTCTCGATGCCCATATGGCATTTGGAGGTCCTTAAG |

TABLE 4-continued

| SEQ ID NO: | Primer | Sequence (5'-3') |
|---|---|---|
| 17 | Primer 13 | CTTAAGGACCTCCAAATGCCATATGGGCATCGAG ACCATTGAT |
| 18 | Primer 14 | TCTAGATGGAACCGTTGCAACCAC |

PCR was performed using the WT chromosome as a template and using the primers of SEQ ID NOs: 15 and 16 and SEQ ID NOs: 17 and 18. PCR was performed under the following conditions. After denaturation at 95° C. for 5 minutes, cycles of denaturation at 95° C. for 30 seconds, annealing at 55° C. for 30 seconds, and polymerization at 72° C. for 90 seconds were repeated 30 times, and then polymerization was performed at 72° C. for 7 minutes. As a result, a DNA fragment of 512 bp of 5' upstream region of the metY gene and a DNA fragment of 520 bp of 3' downstream region of the metY gene were obtained.

PCR was performed using the two amplified DNA fragments as templates and the primers of SEQ ID NOs: 15 and 18. PCR was performed under the following conditions. After denaturation at 95° C. for 5 minutes, cycles of denaturation at 95° C. for 30 seconds, annealing at 55° C. for 30 seconds, and polymerization at 72° C. for 3 minutes were repeated 30 times, and then polymerization was performed at 72° C. for 7 minutes. As a result, a DNA fragment of 1032 bp including only upstream and downstream ends of the metY gene with a deleted central region thereof was amplified.

A pDZ vector and the DNA fragment of 1032 bp were treated with the restriction enzyme XbaI, ligated using a DNA ligase, and cloned to obtain a plasmid which was named pDZ-ΔmetY.

The pDZ-ΔmetY vector was introduced into the prepared WT ΔmetB strain by an electric-pulse method and transformed strains were obtained from a medium for selection including 25 mg/L of kanamycin. The selected strains were subjected to a secondary recombination process of cross-over to obtain WT ΔmetBΔmetY strain in which the metY gene was deleted by the DNA fragment inserted into the chromosome.

In order to prepare a vector for introduction of a mutation into a lysC gene (SEQ ID NO: 20) encoding a WT-derived aspartokinase (SEQ ID NO: 19) to maximize production of O-succinyl homoserine, a primer pair (SEQ ID NOs: 21 and 22) for amplification of 5' upstream region of a mutation site and a primer pair (SEQ ID NOs: 23 and 24) for amplification of 3' downstream region of the mutation site were designed. An XbaI restriction enzyme site (underlined) was inserted to ends of each of the primers of SEQ ID NOs: 21 and 24, and the primers of SEQ ID NOs: 22 and 23 were arranged to place nucleotide substitution (underlined) at sites designed to cross over each other.

TABLE 5

| SEQ ID NO: | Primer | Sequence (5'-3') |
|---|---|---|
| 21 | Primer 15 | tcctctagaGCTGCGCAGTGTTGAATACG |
| 22 | Primer 16 | CACCGACATCATCTTCACCTGCC |
| 23 | Primer 17 | GGCAGGTGAAGATGATGTCGGTG |
| 24 | Primer 18 | gactctagaGTTCACCTCAGAGACGATTA |

PCR was performed using a WT chromosome as a template and using the primers of SEQ ID NOs: 21 and 22 and SEQ ID NOs: 23 and 24. PCR was performed under the following conditions. After denaturation at 95° C. for 5 minutes, cycles of denaturation at 95° C. for 30 seconds, annealing at 55° C. for 30 seconds, and polymerization at 72° C. for 30 seconds were repeated 30 times, and then polymerization was performed at 72° C. for 7 minutes. As a result, a DNA fragment of 509 bp of 5' upstream region of the mutation of the lysC gene and a DNA fragment of 520 bp of 3' downstream region of the mutation of the lysC gene were obtained.

PCR was performed using the two amplified DNA fragments as templates and the primers of SEQ ID NOs: 21 and 24. PCR was performed under the following conditions. After denaturation at 95° C. for 5 minutes, cycles of denaturation at 95° C. for 30 seconds, annealing at 55° C. for 30 seconds, and polymerization at 72° C. for 60 seconds were repeated 30 times, and then polymerization was performed at 72° C. for 7 minutes. As a result, a DNA fragment of 1011 bp including a mutated lysC gene (SEQ ID NO: 26) encoding an aspartokinase mutant (SEQ ID NO: 25) in which threonine at position 311 was substituted with isoleucine was amplified.

A pDZ vector (Korean Patent No. 0924065) unable to replicate in *Corynebacterium glutamicum* and the DNA fragment of 1011 bp were treated with the restriction enzyme XbaI, ligated using a DNA ligase, and cloned to obtain a plasmid which was named pDZ-lysC(T311I).

The pDZ-lysC(T311I) vector was introduced into the WT ΔmetBΔmetY by an electric-pulse method (Appl. Microbiol. Biothcenol. (1999) 52:541-545) and transformed strains were obtained from a medium for selection including 25 mg/L of kanamycin. The selected strains were subjected to a secondary recombination process of cross-over to obtain WT ΔmetBΔmetY, lysC(T311I) strain in which the nucleotide mutation was introduced into the lysC gene by the DNA fragment inserted into the chromosome, and the strain was named *Corynebacterium glutamicum* WT ΔmetBΔmetY, lysC(T311I).

The pECCG117-metX WT, the pECCG117-metX WT_L313R, and pECCG117-metX WT_Q176N_L313R vector prepared in Examples 1 and 2 were introduced into the prepared WT ΔmetBΔmetY by an electric-pulse method and were smeared into a medium for selection including 25 mg/L of kanamycin to obtain transformed strains.

For comparison of O-acetyl homoserine (O-AH)-producing capabilities and O-succinyl homoserine (O—SH)-producing capabilities of the prepared strains, the strains were cultured in the following method and concentrations of O-acetyl homoserine and O-succinyl homoserine in culture media were analyzed.

1 platinum loop of each strain was inoculated onto a 250 ml corner-baffled flask containing 25 ml of the following medium and cultured while shaking at 37° C. at 200 rpm for 20 hours. Concentrations of O-acetyl homoserine and O-succinyl homoserine were analyzed by high performance liquid chromatography (HPLC), and the analyzed concentrations are shown in Table 6.

<Composition of Culture Medium (pH 7.0)>

100 g of glucose, 40 g of $(NH_4)_2SO_4$, 2.5 g of soybean protein, 5 g of corn steep solids, 3 g of urea, 1 g of $KH_2PO_4$, 0.5 g of $MgSO_4.7H_2O$, 100 μg of biotin, 1000 μg of thiamine HCl, 2000 μg of calcium-pantothenic acid, 3000 μg of nicotinamide, 30 g of $CaCO_3$, and 0.3 g of L-methionine (based on 1 L of distilled water).

TABLE 6

| Strains | O-acetyl homoserine (g/L) Batch 1 | Batch 2 | Batch 3 | O-succinyl homoserine (g/L) Batch 1 | Batch 2 | Batch 3 |
|---|---|---|---|---|---|---|
| WTΔmetBΔmetY, lysC(T311I)/ pECCG117-metXWT | 2.0 | 2.2 | 2.1 | 0.01 | 0.03 | 0.01 |
| WTΔmetBΔmetY, lysC(T311I)/ pECCG117-metXWT_L313R | 0.05 | 0.06 | 0.04 | 1.2 | 1.1 | 1.0 |
| WTΔmetBΔmetY, lysC(T311I)/ pECCG117-metX WT_Q176N_L313R | 0.03 | 0.01 | 0.02 | 1.4 | 1.6 | 1.7 |

Referring to Table 6 above, it was confirmed that while O-acetyl homoserine was produced by the strain into which the control metX WT plasmid was introduced, O-succinyl homoserine was produced by the both strains into which the metX mutated plasmids were introduced. Particularly, it was confirmed that production of O-succinyl homoserine was significantly increased in the case of metX WT_Q176N_L313R. That is, the strains into which the mutation was introduced had changed substrate specificity of transferase, thereby producing O-succinyl homoserine.

Example 4: Preparation of MetX Mutation by Saturated Mutagenesis and Evaluation of O-acetyl Homoserine-producing Capability In order to prepare a mutant of MetX, which has high O-succinyl homoserine-producing capability, mutated by substituting an amino acid at position 176 with another amino acid, saturated mutagenesis was used. 18 types of mutants in which an amino acid at position 313 was substituted with arginine and an amino acid at position 176 was substituted with another amino acid were prepared using the plasmid prepared in Example 1 as a template. Variants, substituted amino acids, and sequence numbers of the primers used in the respective variants are shown in Table 7 below.

TABLE 7

| Mutated plasmid | Amino acid substitution | Primer SEQ ID NO: |
|---|---|---|
| 313 mutation | L313R | SEQ ID NO: 9, 10 |
| L313R & 176 mutation | Q176N, L313R | SEQ ID NO: 7, 8 |
| | Q176F, L313R | SEQ ID NO: 27, 28 |
| | Q176S, L313R | SEQ ID NO: 29, 30 |
| | Q176Y, L313R | SEQ ID NO: 31, 32 |
| | Q176C, L313R | SEQ ID NO: 33, 34 |
| | Q176P, L313R | SEQ ID NO: 35, 36 |
| | Q176H, L313R | SEQ ID NO: 37, 38 |
| | Q176L, L313R | SEQ ID NO: 39, 40 |
| | Q176I, L313R | SEQ ID NO: 41, 42 |
| | Q176T, L313R | SEQ ID NO: 43, 44 |
| | Q176R, L313R | SEQ ID NO: 45, 46 |
| | Q176K, L313R | SEQ ID NO: 47, 48 |
| | Q176V, L313R | SEQ ID NO: 49, 50 |
| | Q176A, L313R | SEQ ID NO: 51, 52 |
| | Q176D, L313R | SEQ ID NO: 53, 54 |
| | Q176E, L313R | SEQ ID NO: 55, 56 |
| | Q176G, L313R | SEQ ID NO: 57, 58 |
| | Q176W, L313R | SEQ ID NO: 59, 60 |

Specifically, a variant metX gene was prepared using the primers shown in Table 2 and a site-directed mutagenesis kit (Stratagene, USA). The prepared mutated plasmid was introduced into WTΔmetBΔmetY, lysC(T3111) strains, and then flask evaluation was performed in the same manner as in Example 4. The results are shown in Table 8 below.

TABLE 8

| Strains | Mutation site | O-acetyl homoserine (g/L) Batch 1 | Batch 2 | Batch 3 | O-succinyl homoserine (g/L) Batch 1 | Batch 2 | Batch 3 |
|---|---|---|---|---|---|---|---|
| WTΔmetBΔmetY, lysC(T311I)/ pECCG117-metXWT | | 2.0 | 2.2 | 2.1 | 0.01 | 0.03 | 0.01 |
| WTΔmetBΔmetY, lysC(T311I)/ pECCG117-metX WT_L313R SEQ ID NO: 61 | L313R | 0.05 | 0.06 | 0.04 | 1.2 | 1.1 | 1.0 |
| WTΔmetBΔmetY, lysC(T311I)/ pECCG117-metX WT_Q176N_L313R SEQ ID NO: 63 | Q176N, L313R | 0.03 | 0.01 | 0.02 | 1.4 | 1.6 | 1.7 |
| WTΔmetBΔmetY, lysC(T311I)/ pECCG117-metX WT_Q176F_L313R SEQ ID NO: 65 | Q176F, L313R | 2.1 | 2.1 | 2.2 | 0.01 | 0.02 | 0.01 |

TABLE 8-continued

| Strains | Mutation site | O-acetyl homoserine (g/L) Batch 1 | O-acetyl homoserine (g/L) Batch 2 | O-acetyl homoserine (g/L) Batch 3 | O-succinyl homoserine (g/L) Batch 1 | O-succinyl homoserine (g/L) Batch 2 | O-succinyl homoserine (g/L) Batch 3 |
|---|---|---|---|---|---|---|---|
| WTΔmetBΔmetY, lysC(T311I)/ pECCG117-metX WT_Q176S_L313R SEQ ID NO: 67 | Q176S, L313R | 2.0 | 2.0 | 2.2 | 0.02 | 0.03 | 0.02 |
| WTΔmetBΔmetY, lysC(T311I)/ pECCG117-metX WT_Q176Y_L313R SEQ ID NO: 69 | Q176Y, L313R | 2.1 | 2.2 | 2.2 | 0.01 | 0.01 | 0.02 |
| WTΔmetBΔmetY, lysC(T311I)/ pECCG117-metX WT_Q176C_L313R SEQ ID NO: 71 | Q176C, L313R | 2.0 | 2.1 | 1.9 | 0.04 | 0.01 | 0.03 |
| WTΔmetBΔmetY, lysC(T311I)/ pECCG117-metX WT_Q176P_L313R SEQ ID NO: 73 | Q176P, L313R | 2.1 | 1.9 | 2.1 | 0.01 | 0.03 | 0.01 |
| WTΔmetBΔmetY, lysC(T311I)/ pECCG117-metX WT_Q176H_L313R SEQ ID NO: 75 | Q176H, L313R | 1.6 | 1.3 | 1.6 | 0.1 | 0.3 | 0.1 |
| WTΔmetBΔmetY, lysC(T311I)/ pECCG117-metX WT_Q176L_L313R SEQ ID NO: 77 | Q176L, L313R | 2.2 | 2.1 | 1.9 | 0.01 | 0.02 | 0.05 |
| WTΔmetBΔmetY, lysC(T311I)/ pECCG117-metX WT_Q176I_L313R SEQ ID NO: 79 | Q176I, L313R | 2.0 | 2.3 | 2.1 | 0.01 | 0.02 | 0.02 |
| WTΔmetBΔmetY, lysC(T311I)/ pECCG117-metX WT_Q176T_L313R SEQ ID NO: 81 | Q176T, L313R | 2.2 | 1.7 | 2.1 | 0.01 | 0.04 | 0.01 |
| WTΔmetBΔmetY, lysC(T311I)/ pECCG117-metX WT_Q176R_L313R SEQ ID NO: 83 | Q176R, L313R | 2.0 | 2.0 | 1.9 | 0.05 | 0.03 | 0.06 |
| WTΔmetBΔmetY, lysC(T311I)/ pECCG117-metX WT_Q176K_L313R SEQ ID NO: 85 | Q176K, L313R | 2.2 | 2.2 | 2.1 | 0.01 | 0.00 | 0.01 |
| WTΔmetBΔmetY, lysC(T311I)/ pECCG117-metX WT_Q176V_L313R SEQ ID NO: 87 | Q176V, L313R | 2.0 | 2.2 | 1.9 | 0.05 | 0.01 | 0.02 |
| WTΔmetBΔmetY, lysC(T311I)/ pECCG117-metX WT_Q176A_L313R SEQ ID NO: 89 | Q176A, L313R | 2.1 | 1.9 | 1.9 | 0.01 | 0.03 | 0.03 |
| WTΔmetBΔmetY, lysC(T311I)/ pECCG117-metX WT_Q176D_L313R SEQ ID NO: 91 | Q176D, L313R | 2.0 | 1.8 | 2.1 | 0.04 | 0.06 | 0.08 |
| WTΔmetBΔmetY, lysC(T311I)/ pECCG117-metX WT_Q176E_L313R SEQ ID NO: 93 | Q176E, L313R | 1.9 | 1.9 | 2.0 | 0.07 | 0.02 | 0.05 |

TABLE 8-continued

| Strains | Mutation site | O-acetyl homoserine (g/L) Batch 1 | Batch 2 | Batch 3 | O-succinyl homoserine (g/L) Batch 1 | Batch 2 | Batch 3 |
|---|---|---|---|---|---|---|---|
| WTΔmetBΔmetY, lysC(T311I)/ pECCG117-metX WT_Q176G_L313R SEQ ID NO: 95 | Q176G, L313R | 1.4 | 1.2 | 1.4 | 0.2 | 0.4 | 0.1 |
| WTΔmetBΔmetY, lysC(T311I)/ pECCG117-metX WT_Q176W_L313R SEQ ID NO: 97 | Q176W, L313R | 0.1 | 0.08 | 0.07 | 1.0 | 1.1 | 1.3 |

Referring to Table 8, it was confirmed that while most of the mutants were unable to produce O-succinyl homoserine, mutated metX (L313R, Q176N), (L313R, Q176W), (L313R, Q176H), or (L313R, Q176G) produced O-succinyl homoserine with a high level compared to wild type, respectively. That is, it was confirmed that when the amino acid at position 313 of the amino acid sequence of SEQ ID NO: 1 is substituted with arginine, and the amino acid at position 176 thereof is substituted with asparagine, tryptophan, histidine, or glycine, substrate specificity to succinyl CoA is provided to the transferase, thereby producing O-succinyl homoserine.

The above-described results show that the mutant according to the present disclosure may increase production of O-succinyl homoserine.

In addition, the prepared WTΔmetBΔmetY,lysC(T311I)/pECCG117-metX WT_Q176N_L313R strains and WT_ΔmetBΔmetY, lysC(T311I)/pECCG117-metX WT_Q176W_L313R strains are designated as CA05-5136 and CA05-5137, respectively and deposited under the Budapest Treaty to the Korean Culture Center of Microorganisms (KCCM) on May 11, 2017, with Accession Nos. KCCM12024P and KCCM12025P.

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

Deposition Number

Depositary Authority: Korea Culture Center of Microorganisms (KCCM)

Accession number: KCCM12024P

Date of deposit: May 11, 2017

Depositary Authority: Korea Culture Center of Microorganisms (KCCM)

Accession number: KCCM12025P

Date of deposit: May 11, 2017

The invention claimed is:

1. An isolated variant polypeptide having O-succinyl homoserine transferase activity, which comprises a substitution of an amino acid at position 313 in the amino acid sequence of SEQ ID NO: 1 with arginine and a substitution of an amino acid at position 176 in the amino acid sequence of SEQ ID NO: 1 with an amino acid other than glutamine and wherein the variant has at least 90% sequence identity to SEQ ID NO:1.

2. The isolated polypeptide of claim 1, wherein the amino acid at position 176 is substituted with asparagine, tryptophan, histidine, or glycine.

3. The isolated polypeptide of claim 1, wherein the polypeptide comprises at least one amino acid sequence selected from the group consisting of amino acid sequences of SEQ ID NOs: 63, 75, 95, and 97.

4. An isolated polynucleotide encoding the polypeptide having the O-succinyl homoserine transferase activity of claim 1.

5. The isolated polynucleotide of claim 4, wherein the polynucleotide comprises at least one nucleic acid sequence selected from the group consisting of nucleic acid sequences of SEQ ID NOs: 64, 76, 96, and 98.

6. A microorganism of the genus *Corynebacterium* producing O-succinyl homoserine, wherein the microorganism comprises the polypeptide having the O-succinyl homoserine transferase activity of claim 1 or a mutant polypeptide thereof or wherein, in the microorganism, the polypeptide having the O-succinyl homoserine transferase activity of claim 1 or a mutant polypeptide thereof is overexpressed.

7. The microorganism of claim 6, wherein the microorganism of the genus *Corynebacterium* has further enhanced aspartokinase activity compared to non-mutated microorganisms.

8. The microorganism of claim 6, wherein the microorganism of the genus *Corynebacterium* is *Corynebacterium glutamicum.*

9. The microorganism of claim 6, wherein activity of at least one enzyme selected from the group consisting of cystathionine synthase, O-acetyl homoserine (thiol)-lyase, and homoserine kinase is inactivated in the microorganism of the genus *Corynebacterium.*

10. The microorganism of claim 6, wherein the microorganism of the genus *Corynebacterium* has further enhanced aspartokinase activity compared to non-mutated microorganisms and activity of at least one enzyme selected from the group consisting of cystathionine synthase, O-acetyl homoserine (thiol)-lyase, and homoserine kinase is inactivated.

11. A method of producing O-succinyl homoserine, the method comprising:

culturing a microorganism of the genus *Corynebacterium* producing O-succinyl homoserine according to claim 6 in a culture medium; and separating or recovering O-succinyl homoserine from the microorganism cultured in the culturing step or the culture medium.

12. A method of producing L-methionine, the method comprising:

(a) culturing a microorganism of the genus *Corynebacterium* producing O-succinyl homoserine according to claim 6 in a culture medium; and (b) reacting the O-succinyl homoserine with a sulfide.

13. The method of claim 12, further comprising separating or recovering O-succinyl homoserine from the cultured microorganism or the culture medium in step (a).

14. The method of claim 12, further comprising separating or recovering L-methionine produced by the reaction between O-succinyl homoserine and the sulfide in step (b).

* * * * *